United States Patent [19]
Heiman

[11] Patent Number: 5,290,269
[45] Date of Patent: Mar. 1, 1994

[54] HYGIENIC PRODUCTS AND FABRICS THEREFOR

[75] Inventor: Mark J. Heiman, Maineville, Ohio

[73] Assignee: Standard Textile Co., Inc., Cincinnati, Ohio

[21] Appl. No.: 646,661

[22] Filed: Jan. 25, 1991

Related U.S. Application Data

[63] Continuation-in-part of Ser. No. 424,538, Oct. 20, 1989, abandoned.

[51] Int. Cl.⁵ .................. A61F 13/46; A61F 13/54; A61F 13/56
[52] U.S. Cl. .................. 604/378; 604/384; 604/386; 604/374; 604/372; 604/385.1
[58] Field of Search .......... 604/374, 377, 378, 384, 604/386, 387, 366, 371, 372, 385.1

[56] References Cited

U.S. PATENT DOCUMENTS

| | | | |
|---|---|---|---|
| 2,290,110 | 7/1942 | McGraw | 604/385.1 |
| 3,367,333 | 2/1968 | Scheier | 604/378 X |
| 3,561,441 | 2/1971 | Lombardi | 604/378 X |
| 3,768,479 | 10/1973 | Widlund | 604/366 |
| 3,882,871 | 5/1975 | Taniguchi | 604/371 X |
| 3,955,575 | 5/1976 | Okuda | 604/391 |
| 4,029,100 | 6/1977 | Karami | 604/374 X |
| 4,195,634 | 4/1980 | DiSalvo et al. | 604/366 |
| 4,216,774 | 8/1980 | Graber | 604/371 |
| 4,315,507 | 2/1982 | Whitehead et al. | 604/387 X |
| 4,333,463 | 6/1982 | Holtman | 604/378 X |
| 4,704,117 | 11/1987 | Mitchell | 604/391 |
| 4,798,603 | 1/1989 | Meyer et al. | 604/378 |
| 4,855,139 | 8/1989 | Srinivasan | 604/374 X |
| 4,865,597 | 9/1989 | Mason et al. | 604/385.1 |
| 4,875,492 | 10/1989 | Mitchell et al. | 604/378 X |

FOREIGN PATENT DOCUMENTS

| | | | |
|---|---|---|---|
| 1192701 | 9/1985 | Canada | 604/387 |
| 2597123 | 10/1987 | France | 128/78 |
| 0088903 | 5/1984 | Japan | 604/385.1 |

*Primary Examiner*—Randall L. Green
*Assistant Examiner*—Willse David H.
*Attorney, Agent, or Firm*—Kinney & Schenk

[57] ABSTRACT

A knit terry fabric having hydrophobic/hydrophilic characteristics provides hygienic panels for washable, reusable, incontinent pads and diapers. In one embodiment, a non-woven fabric, stiffener sheet is employed in an incontinent pad to resist its being folded in use. The diaper embodiment employs a Y-shaped configuration and is provided with preventing Velcro fasteners from being fouled during washing.

99 Claims, 8 Drawing Sheets

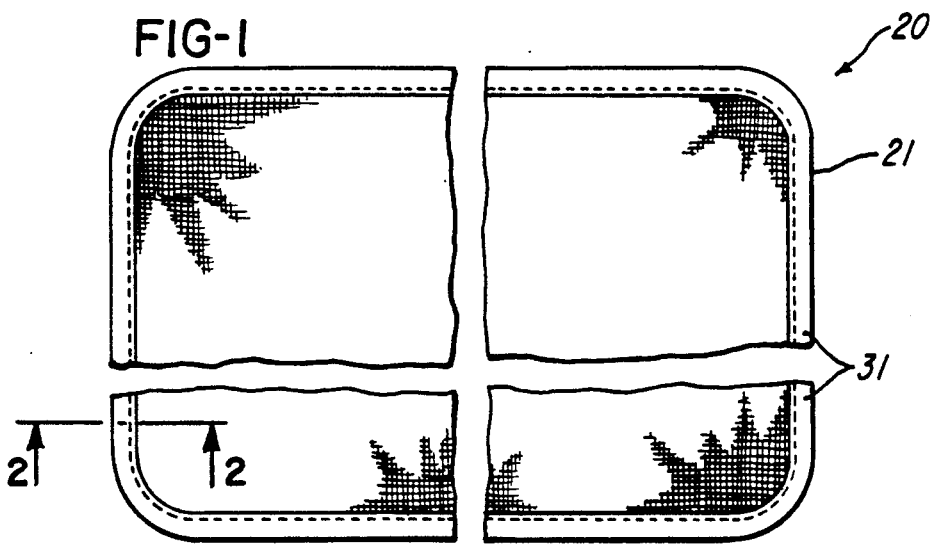
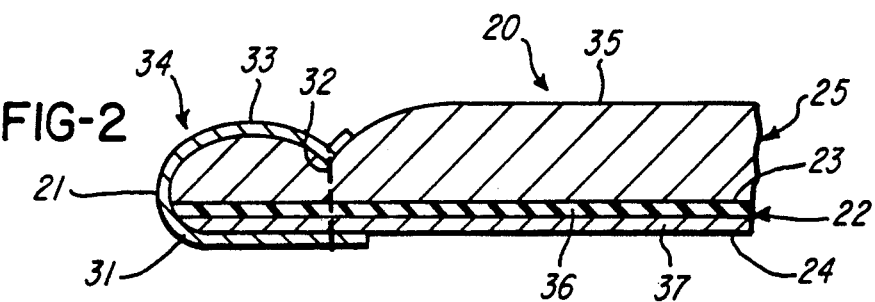
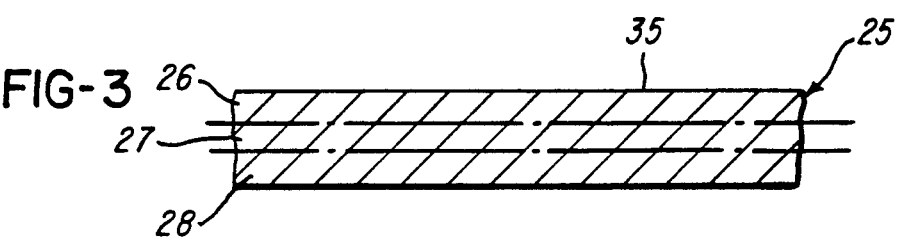
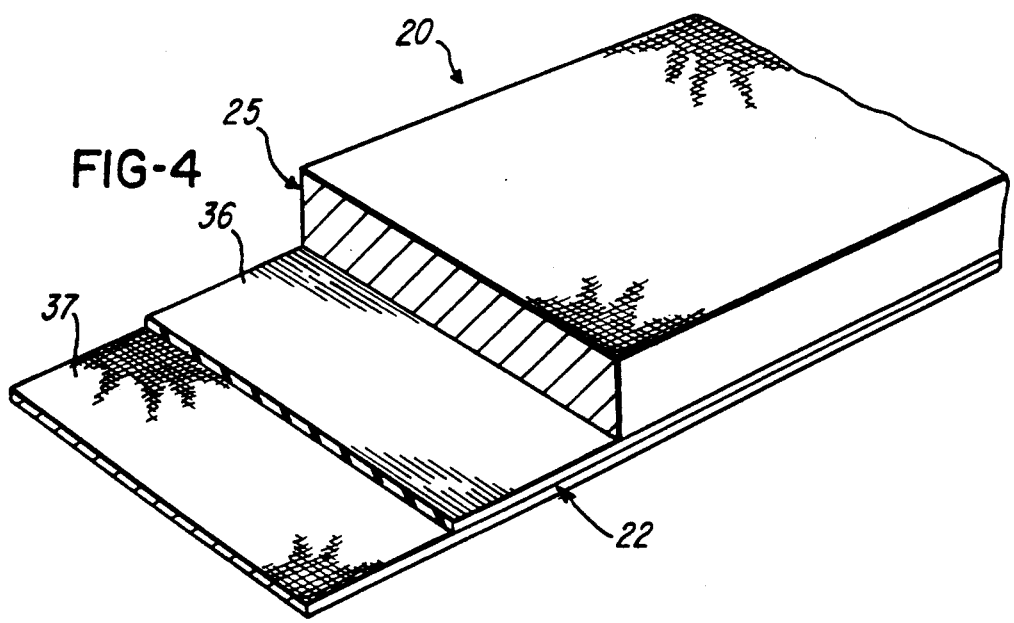

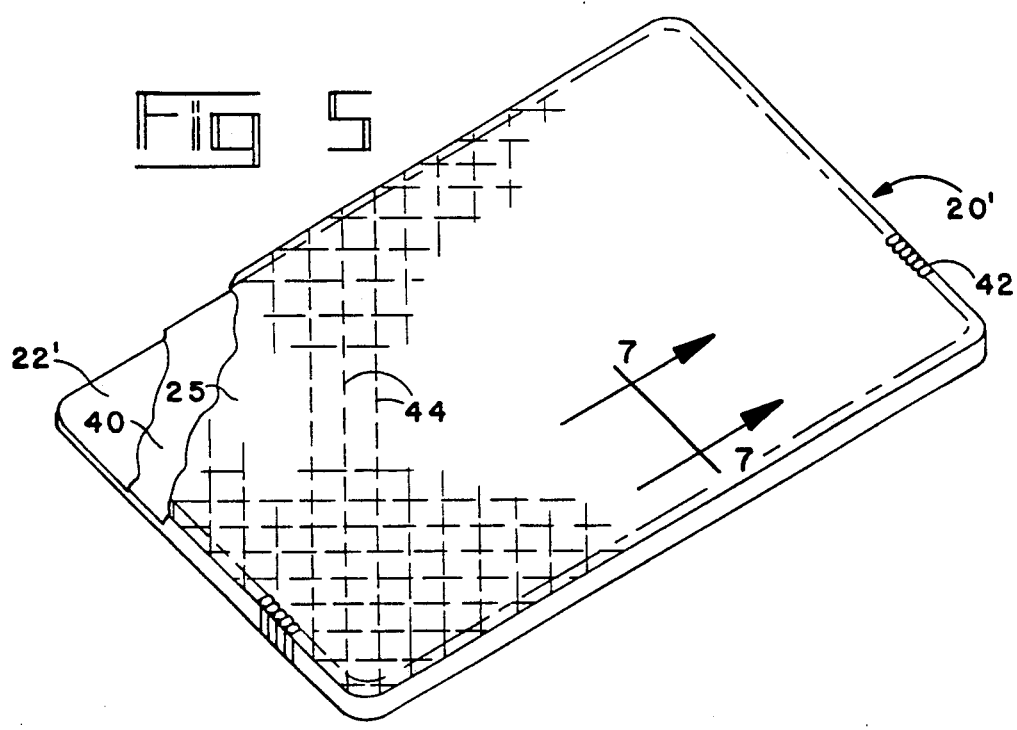
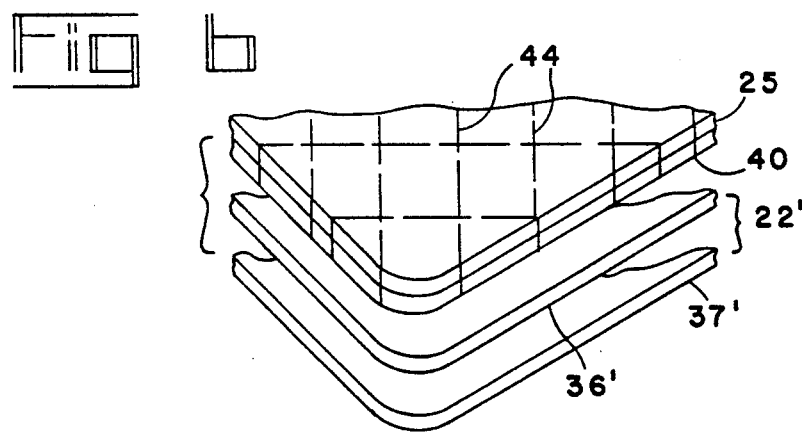
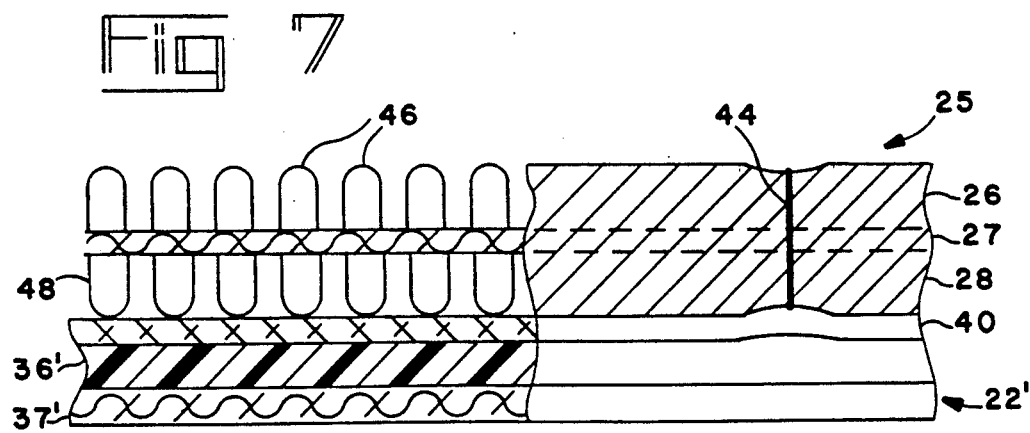

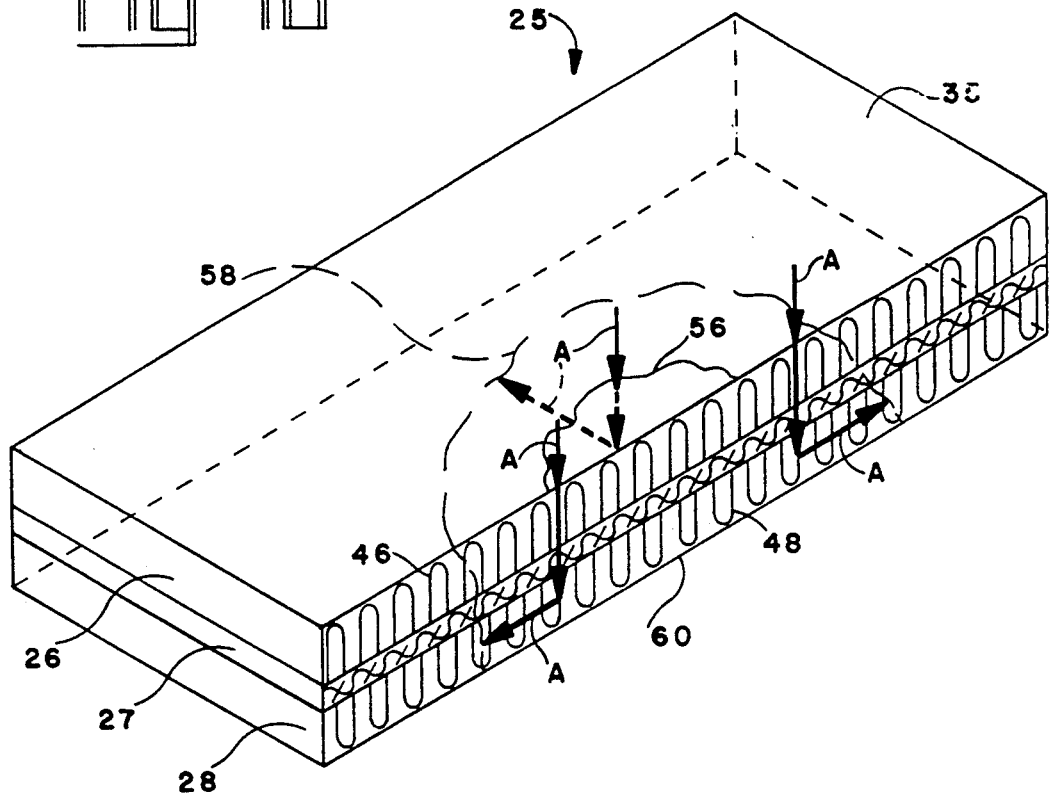

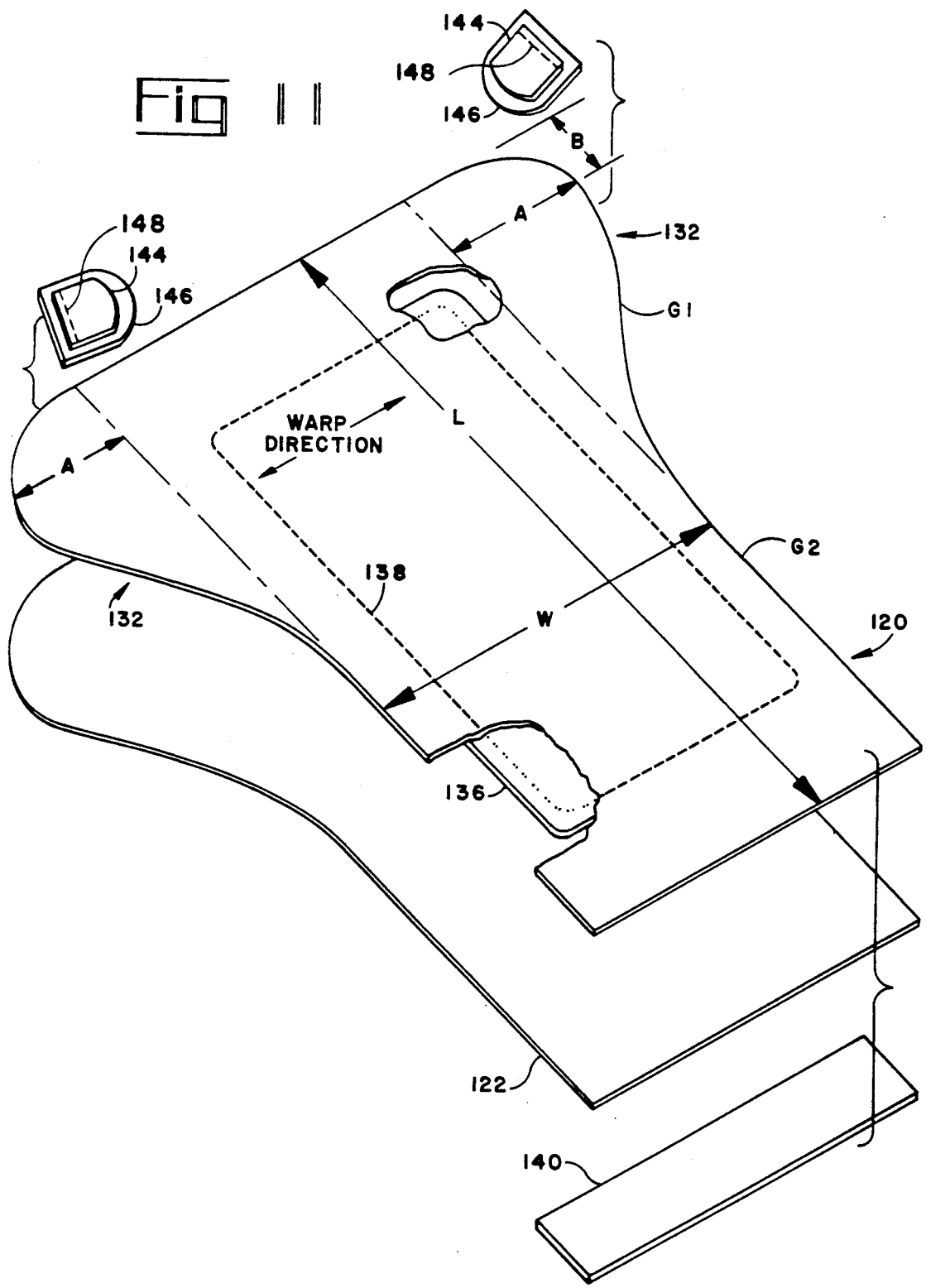

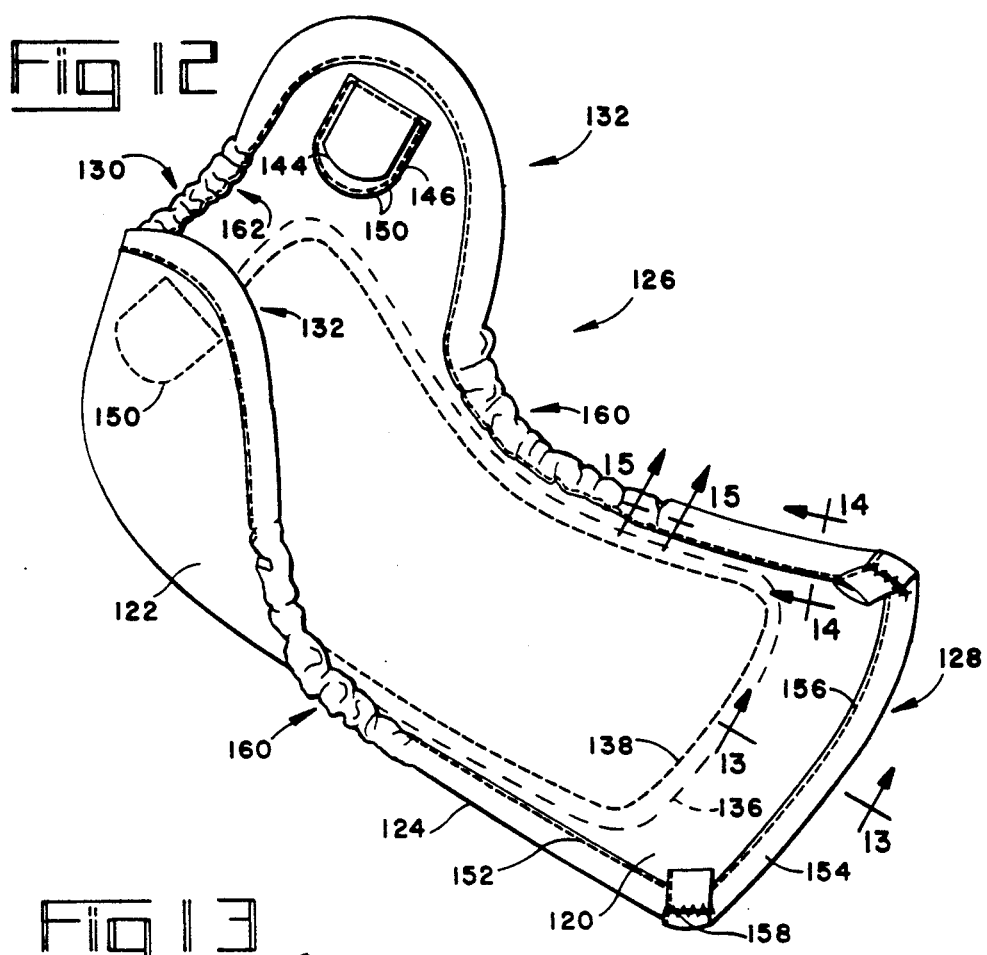
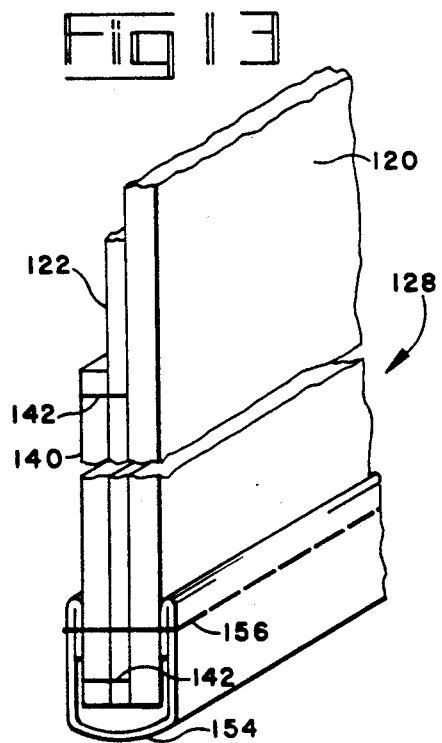
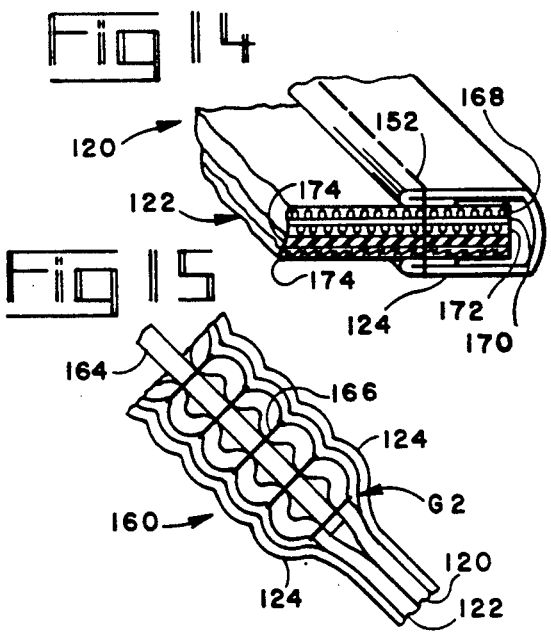

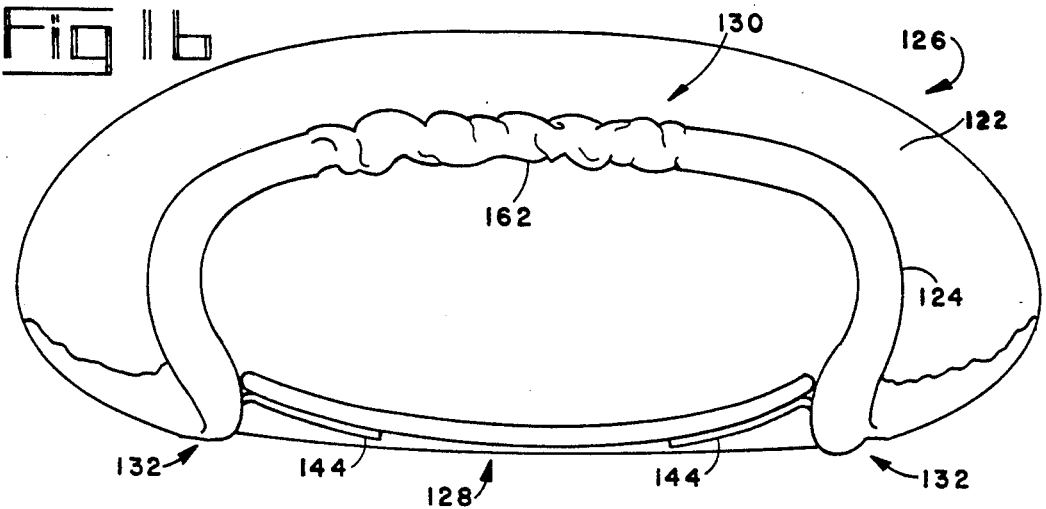
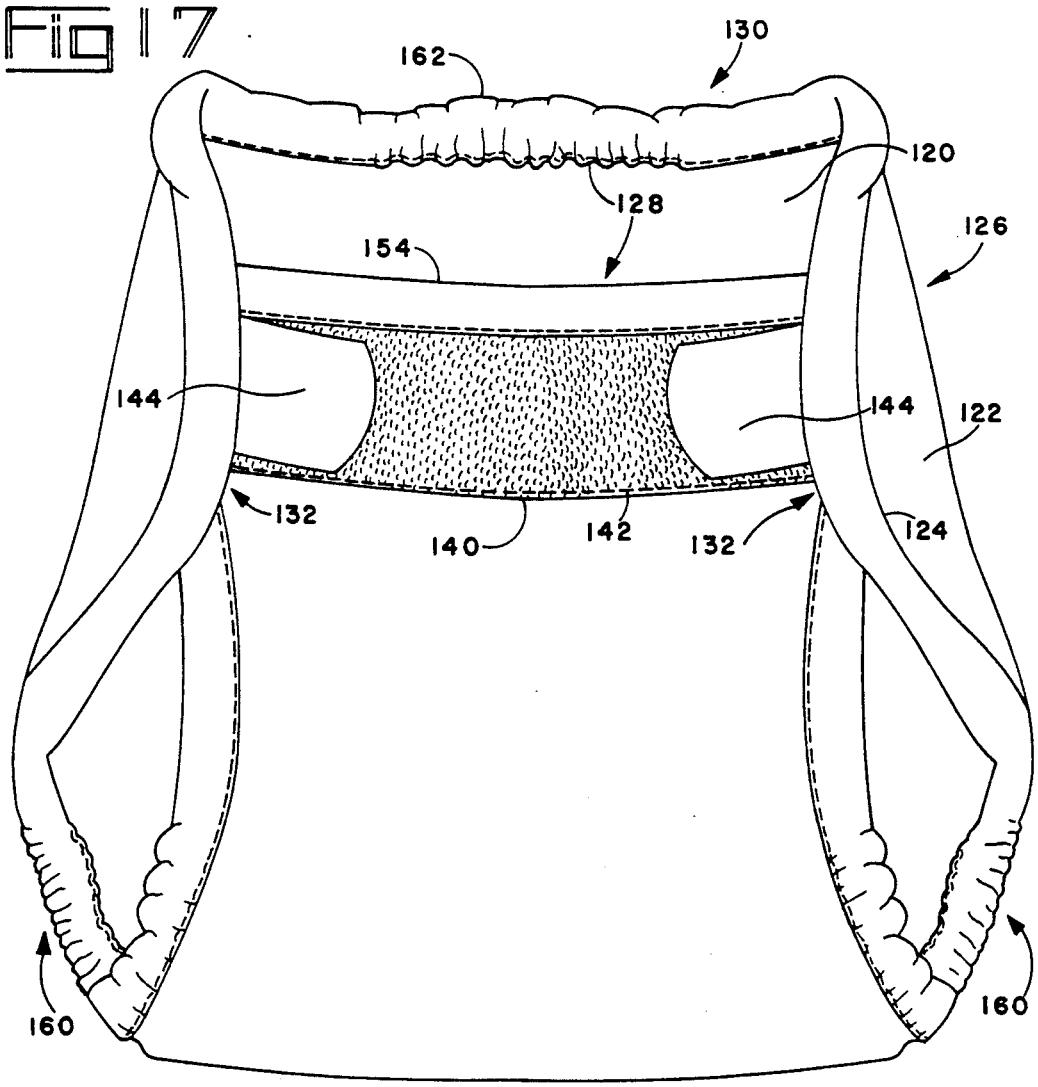

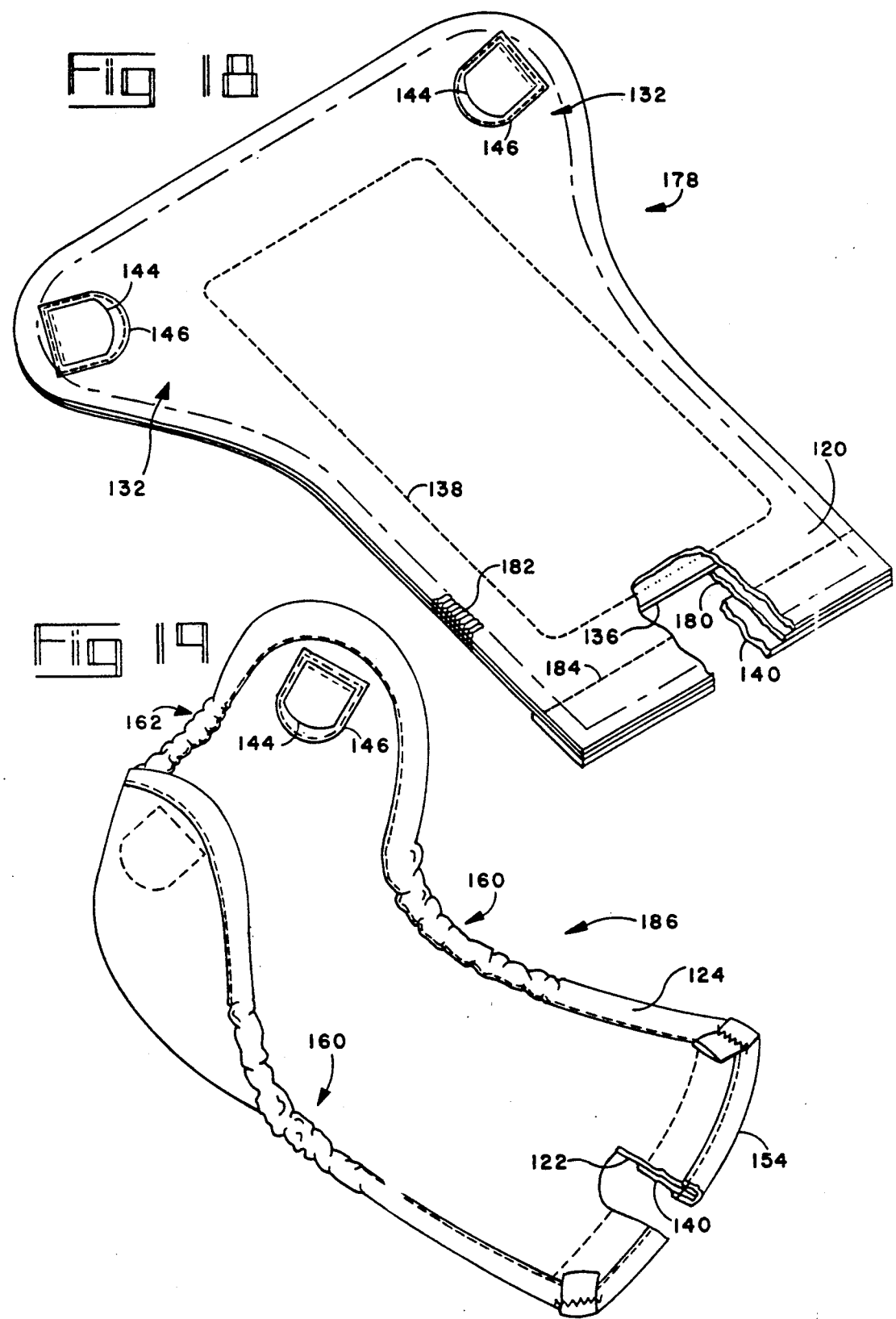

HYGIENIC PRODUCTS AND FABRICS THEREFOR

This application is a continuation in part of application Ser. No. 424,538 filed Oct. 20, 1989, now abandoned.

The present invention relates to improvements in hygienic products, exemplified by diapers and incontinent pads, and improved fabrics therefor.

While not necessarily so limited, the present invention is further directed to improvements in washable diapers and incontinent pads, which are thereby capable of repetitive reuse.

The management of human wastes, specifically urine and feces, has long posed a challenge and, literally, a myriad of solutions have been proposed, as is evidenced by the fast number of prior patents which have heretofore proposed solutions, each of which has some shortcoming.

Basically the problem being dealt with it incontinency, i.e., the uncontrolled discharge of urine or feces. This is a universal problem in infants, which continues until a stage of maturity is reached at which muscular control is developed to a point where such discharge is capable of being controlled by the individual. Incontinency is also a serious problem for adults, particularly the elderly, who loose voluntarily control over the discharge of such wastes, either temporarily or chronically, due to some form of muscular or neurological infirmity.

The basic functions of such hygienic products are to minimize skin wetness and to prevent spread of the waste products. Because urine is a free flowing liquid, it spreads more readily than feces, and its management, is thus more difficult. For this reason, reference will be made, herein, primarily to features relating to urine management. It is to be appreciated that those features will also be applicable to the liquid portion of feces.

Although not discussed in detail herein, it will also be apparent that the term hygienic products include devices used in the management of other body fluids, such as blood, and that the present teaching are applicable thereto.

Hygienic products, for the management of body wastes, take two, basic forms, one being what is termed an incontinent pad and the other being in the form of a garment, which is known as a diaper.

Incontinent pads are, primarily, used to protect bed clothing where the incontinent is non-ambulatory, or incontinency is primarily a night time problem. Basically, an incontinent pad comprises an absorbent hygienic panel which is used in combination with what will be, herein, referenced as a barrier sheet, i.e., a flexible, liquid impervious sheet. One practice is to place a "rubber" (barrier) sheet on a mattress and then to place the absorbent panel on the "rubber" sheet. The incontinent then lies on the absorbent panel, which has sufficient lateral extent to absorb discharged urine and prevent its free flow beyond the underlying rubber sheet. Alternatively, the barrier sheet and absorbent hygienic panel may have identical outlines and be secured together to form an unitary, incontinent pad which provides both hygienic and protective functions. Incontinent pads may also be in the form of a chair pad, to prevent damage to the chair, or floor, when an incontinent is sitting thereon.

The separate hygienic panel, or the unitary incontinent pad is periodically replaced, as required, to thereby minimize the extent to which the incontinent's skin is wet, as well as to prevent spread of urine which might exceed the absorbent capability of the hygienic panel. The use of a unitary incontinent pad gives the advantage of providing both a clean hygienic panel and a clean barrier sheet each time it is replaced.

Diapers serve the same hygienic function as incontinent pads but differ, primarily, in that they are in the form of a garment, which is worn by an incontinent. Thus, a diaper comprises an absorbent, hygienic panel, which embraces the crotch of the incontinent, with end portions being secured at the incontinent's waist to maintain it in place. Alternate constructions are also employed, as by the use of fastening means in the crotch portion. A barrier sheet then overlies the hygienic panel to prevent spread of urine. The barrier sheet may be a separate item, exemplified by "rubber pants", which is put on the incontinent after the hygienic panel is secured to embrace the crotch area. Alternatively, the barrier sheet is secured to the hygienic panel to form a unitary, or one piece diaper, which provides both hygienic and protective functions. It is also to be appreciated that the hygienic panel may be used alone, as where the incontinent, particularly an infant, is placed on a rubber sheet, which then provides the protective function.

As indicated above, a primary problem in the management of an incontinent's urine is minimizing the extent to which his skin is wet. Skin wetness, or direct exposure to urine, in a worst case, can be the cause of debilitating lesions, and, in any event is a cause of discomfort, which is evidenced, for example, by a baby's crying. While skin wetness can be minimized by increasing the absorbent capacity of the hygienic panel, as by increasing its thickness, an absorbent material, contacting the incontinent's skin, inherently maintains some degree of skin wetness.

This inherent property of an absorbent material is well recognized and, relatively recently, an effective solution to this problem has been found in the provision of hygienic panels which have a top, hydrophobic surface portion, which is in contact with the incontinent's body. (For sake of convenience and uniformity, the terms "top" or "upper" denote the portion, or surface of the incontinent product in contact with or nearest to the person of the incontinent. The terms "bottom" or "lower" denote the portion, or surface of the product remote from, or outwardly of the person of the incontinent.) Such hygienic panels then have an outer, hydrophilic, portion. Urine is wicked through the hydrophobic portion and then absorbed into the hydrophilic portion which serves a reservoir function, maintaining the urine in spaced relation from the person, or skin surface, of the incontinent. Thus, shortly after a void, there is only a minimal amount of urine retained in the hydrophobic portion, this will quickly dry, so that the incontinent feels dry, and, in fact is dry in that his skin is exposed to urine moisture for a short period of time, and to liquid urine for an ever shorter period of time.

Hygienic products having such hydrophobic/hydrophilic portions are commonly referenced as being, or having, a "dry feel" and that term will be used herein.

At this point it will be noted that there are certain terms, in this art, including "hydrophilic" and "hydrophobic", which are, at times, not used consistently, or which have ambiguous meanings.

As herein used here "hydrophilic" is used in the sense that it denotes an affinity for a liquid, specifically including urine. "Hydrophilic" includes, within the present definition, "absorb", "absorbent" and "absorption", all of which denote the capability of sucking in and/or retaining a liquid, in the nature of the action of a sponge. "Hydrophilic" may also includes "adsorb", adsorbent" and "adsorption", all of which denote an adhesion of liquid in a thin layer to the surface of a solid body.

The latter characteristic is of significance in considering resinous yarns, which are formed of a plurality of filaments, or fibers. To exemplify, polyester is a resinous material which has essentially no capability to "absorb" water, or water based liquids. Further, the surface characteristics of polyester are such that only a minimal amount of liquid will adhere to its surface. Polyester filaments are, per se, hydrophobic, being essentially non-adsorbent and non-absorbent. However, when a yarn is comprised of polyester filaments, interstices are formed, in which liquid will be retained. Further, various surface treatments are available, also known as hydrophilic imparters, which significantly increase the adsorption of, i.e., the capability of liquids to adhere to, the surfaces of polyester fibers. Polyester yarns, so treated, through adsorption, in effect, are absorbent and hydrophilic. A polyester yarn may also be formed by filaments of different deniers to increase the capability of the yarn to absorb liquids, as liquids are adsorbed onto the filament surfaces and thus absorbed into the interstices of the filaments. Polyester, and other polymeric material, yarns can thus be made hydrophilic.

"Hydrophobic", as herein used connotes a repulsion of liquids, specifically including urine. It denotes both non-absorption and non-adsorption characteristics.

It is to be appreciated that the terms hydrophilic and hydrophobic are relative. Thus, a hydrophilic yarn, or layer, can retain some minimal amount of liquid and still be considered hydrophobic. Similarly, a hydrophilic yarn or layer can have varying absorption capacities.

"Wick" and "wicking are related terms, which are herein used to connote a migration of liquid, as opposed to the flow of a stream of liquid. To illustrate, liquid will be drawn into an absorbent yarn and progressively "wick" to portions thereof, which are less saturated.

As further background to the present invention, it will be noted that infant diapers represent a substantial majority of the market of incontinent, hygienic products. In the recent past, there have been intensive efforts to provide single use, disposable infant diapers, which have had widespread commercial acceptance. Much of the developmental effort in improving hydrophobic/hydrophilic, dry fee diapers is linked to disposable diapers.

It is now recognized that use of disposable diapers is environmentally unsound because of the burdens placed on trash disposal systems.

One of the objects of the present invention is minimize trash disposal problems through the provision of reusable, hygienic products. This, inherently, requires that the hygienic product be washable.

Reference has been made to disposable diapers to point out that many of the teachings, relating to the provision of a dry feel, in the disposable diaper art are not applicable to reusable diapers, or other reusable hygienic products. This is to say that the effectiveness of the hydrophobic/hydrophilic portions of disposable diapers is lost when such diaper is washed. The same is true with respect to other disposable hygienic products.

There are numerous prior art teachings of hydrophobic/hydrophilic dry feel, hygienic products or panels.

For the most part, these teachings involve the use of discrete layers of fibrous material, which must be mated in the fabrication of the product, to provide the hydrophobic/hydrophilic properties. The use of discrete layers of fibrous material can present several problems, among which are separation during use or when washed; difficulties in assembly during the fabrication process; and a relatively high cost.

There is one known teachings of a washable, unitary hygienic panel found in U.S. Pat. No. 3,367,333—Scheier. It is there proposed to provide hydrophobic and hydrophilic yarn loops on the same surface of a ground fabric. The hydrophobic loops have a greater height than the hydrophilic loops, thereby providing a hydrophobic upper surface portion. The shorter, hydrophilic loops, being on the same side of the ground fabric, have minimal separation from the skin surface of the incontinent. This arrangement is of limited effectiveness is providing a dry feel, particularly where the incontinent is an adult, whose weight will compress the hydrophobic loops into the hydrophilic loops.

With the foregoing is mind, a primary object of the present invention is to provide improved, washable, reusable hygienic products for incontinents.

A further and more specific object of the present invention is to provide improved, washable, reusable diapers and incontinent pads.

Yet another, related object of the invention is to provide an improved fabric for use as a panel in hygienic products, wherein the fabric, as a unitary article, provides hydrophobic/hydrophilic properties for obtaining a dry feel.

With specific reference to incontinent pads, there is a further problem in that they tend to "bunch up" in use, to the end that they are uncomfortable to the user and/or defeat the protective function for which they are provided.

This problem is particularly apparent where the incontinent pad is used by a bed ridden patient. The pad overlies the bed clothes, with the user resting on the pad. When the user shifts his position, there is a tendency for a portion of the pad to move with the user's body and shift relative to the bed and other portions of the pad. This often results in the pad, or portions thereof, in being folded to a double, or triple thickness, which is uncomfortable to the user. Also, when so folded, the effective area of the pad is decreased, which can result in a void flowing onto the bed, rather than onto the pad.

Accordingly, yet another object of the present invention is to give greater assurance that the effectiveness of incontinent pads will not be defeated by user movement, as well as to assure that user movement will not create an uncomfortable fold in the pad.

Diapers require some means for securing them to the person of the user. Basically, all diapers are, initially, generally flat and are then folded around the person of the user to embrace the crotch area. Portions of the so-folded diaper are overlapped and secured together to hold the diaper in place. Safety pins have been widely used for this purpose.

More recently hook and loop fasteners sold under the trademark Velcro have been widely used to releasably fasten these overlapped diaper portions. Such fasteners comprise a flexible strip, which has "hook" projections, mounted on one member and a loop piece, which comprises a layer of fiber loops and is mounted on another member. The "hook" projections are intermeshed with the fiber loops to hold the two members in assembled relation. A characteristic of this fastening mechanism is that is highly resistant to separation in response to forces parallel to the plane of the intermeshed connection, but is readily capable of being separated in response to a force normal to this plane.

Hook and loop fasteners have enjoyed considerable acceptance in "one piece", disposable diaper constructions, since they can be readily engaged and disengaged and yet provide a secure fastening of the overlapped diaper portions. However, when these fasteners are used in reusable diapers, their effectiveness is reduced because of lint which is generated when they are washed. This is to say that the diaper fabric fibers, or line, tend to be deposited on the fastening elements due to agitation in the washing, as well as the drying, process.

One proposal to overcome this problem is found in U.S. Pat. No. 4,537,591—Coates. It is there proposed to provide a loop piece cover to which the hook piece strap is attached during washing. In effect, the loop piece cover provides a "parking place" for the hook piece strap, during washing.

A further object of the invention is to facilitate the attachment of a hook fastener strap and loop piece to a garment, particularly a diaper, in the provision of a parking place for the strap to protect the latter when the garment is washed.

Another challenge to the design of diaper constructions is to provide a snug fit with the torso of the user and in so doing to avoid user discomfort.

Diapers are required by users of all sizes, from premature infants to obese adults. Obviously, a single size of diaper cannot be adapted for use by users of such diverse proportions. Thus, it is a necessary and accepted practice to provide a serious of diaper sizes. Each diaper size is then adapted to be secured to a relatively small range of user dimensions. At one end of this series of sizes would be the premature baby size, adapted for use with infants having a weight between two or three pounds. At the other end of this series would be the extra large adult size, adapted for use by adults having a weight ranging between, perhaps, 200 and 250 pounds.

Economy considerations dictate that this wide range of user size be accommodated by a minimum number of diaper sizes. This end is, however, difficult to obtain and still provide the desired snug fit. This is to say that conventional diaper configurations limit the range of user weight that can be accommodated by a given diaper size, while still obtaining a snug fit.

Accordingly, a further object of the present invention is to provide an improved diaper configuration which, for a given size, provides a snug fit for a relatively wide range of size, or weight, of incontinents.

There are additional considerations, which are of greater concern in diapers to be used by adult incontinents.

Among these considerations is the fact that most adults have a strong desire to look as normal as possible when wearing a diaper. Because of the bulkiness of present diaper configurations, adult user's are often forced to dress in loose clothing in order to hide the fact that a diaper is being worn. This seriously limits the styles of clothing that an adult incontinent can wear.

An interrelated fact that is that adult voids are, generally, of a relatively large volume. This is further complicated by the fact that weight of most adults is such that urine can be squeezed from weight bearing portions of the absorbent portion of the diaper. This urine is then free to rewet the skin of the user, as well to escape from the protective cover therefor and thus stain clothing, all to the embarrassment of the adult user.

Accordingly, a further object of the invention is to provide an improved diaper construction which minimizes, if not eliminates, the possibility of an adult user being embarrassed.

A more specific object of the invention is to provide a diaper capable of containing voids of a relatively large volume.

A further, related specific object of the present invention is to minimize the skin wetness and to minimize, if not eliminate leakage of urine from the protective cover of the diaper.

Another, related object of the invention is to provide such an improved adult diaper, which has a minimum of bulk, to the end that there is a minimum limitation on the style of clothing which may be worn by the user.

Included within the last identified object, is the end of simplifying the methods for fabrication such diaper constructions.

In accordance with one aspect of the invention, the foregoing ends may be attained by an absorbent textile fabric adapted to provide a dry feel on one surface thereof. This fabric has separate hydrophobic and hydrophilic properties, and comprises a top portion, of finite thickness, the outer portion of which defines the upper surface of the fabric; a bottom portion of finite thickness, the outer portion of which defines the lower surface of the fabric; and a central portion in which the inner portions of the top and bottom portions are intermeshed. The top portion is characterized in that it is hydrophobic; wicks liquid from the upper surface of the fabric to the central portion; and is incapable of retaining any substantial amount of liquid therein. The bottom portion is characterized in that it is hydrophilic; wicks liquid from the central portion into the remainder of the bottom portion; and provides a reservoir function in retaining the liquid. The upper surface of the fabric thus has a dry feel shortly after liquid is discharged thereon.

In accordance with other aspects of the invention, this fabric can be characterized by a top portion comprising yarns having lower ends included int eh ground portion and projecting upwardly therefrom to define the upper surface of the fabric. The bottom portion comprises hydrophilic yarns having upper ends included in the ground portion and projecting upwardly therefrom to define the lower surface of the fabric. The upper ends of the hydrophilic yarns provide means for wicking liquid through the ground layer and into the bottom layer.

In accordance with further aspects of the invention, the novel fabric is preferably a knit terry fabric. The top portion is a piling comprising a plurality of loops formed by top yarns projecting upwardly from the central ground portion, with the outer ends of the loops defining the top surface of the fabric. The bottom portion is a piling comprising a plurality of loops formed by bottom yarns projecting downwardly from the central ground portion, with the outer ends of the loops defining the bottom surface of the fabric. The central portion comprising the inner ends of the top and bottom yarns and ground yarns, all inter-knit in a relatively dense arrangement anchoring the top and bottom piling loops thereto.

The top yarns and the top piling portion are hydrophobic and permit the wicking of liquid, impinged on the top surface of the fabric, to the central ground portion. The bottom yarns and the bottom piling portion are hydrophilic. The inner ends of the hydrophilic, bottom yarns serve to facilitate wicking of liquid through the ground portion for absorption into the bottom portion. The ground yarns may also be hydrophilic to further facilitate wicking of liquid through the ground portion. The ground yarns may comprise resinous fibers which provide additional strength for the ground portion.

Various features contribute to the effectiveness of the this fabric in providing a dry feel, with the ability to absorb and hold, in reservoir fashion, a relatively large volume of liquid. These features are fully discussed in the following description of preferred embodiments and are here briefly identified.

The top portion may be comprised of loops formed of hydrophobic yarn, preferably comprising continuous filaments of polymeric material, preferably a textured, polyester yarn.

The bottom portion may be comprised of uncut loops formed of a hydrophilic yarn, preferably comprising natural fiber staples, preferably cotton.

The central ground portion may comprise the inner ends of the yarn loops forming the top and bottom portions and further may comprise one or more ground yarns. The central ground portion has a relatively high yarn density which provides a separation between the top and bottom portions, whereby liquid is wicked through the central ground portion into the bottom portion, while inhibiting reverse flow of liquid from the bottom portion back to the top portion.

It is further preferred that the top surface of the hydrophobic portion be brushed in order to provide improved user comfort, as well as to facilitate its wicking function.

The preferred weight of this fabric is in the range of 7 to 13.5 ounces per square yard. Within this range there are two preferred fabrics, one having a weight of 7.5 ounces and the other having a weight of 10.5 ounces. Additionally there are preferred weight percentages of hydrophilic and hydrophobic yarns, along with preferred yarn deniers, all of which are identified in the following description.

When incorporated in a hygienic product, liquid impinged on the upper surface of the fabric will pass through the central layer immediately therebeneath and then spread laterally outwardly in the bottom layer, thereby minimizing the lateral spread of liquid in the top portion.

Other ends of the present invention are attained through the use of fabrics, as above characterized, as hygienic panels of hygienic products in general, and diapers and incontinent pads in particular. Such hygienic panels are advantageously employed in combination with a barrier sheet, which contains urine voided by an incontinent and thus protection for clothing, bed clothes, furniture and the like.

Other objects of the invention are attained by a hygienic product in the form of an incontinent pad, or the like, comprising a hygienic panel and an underlying barrier sheet. The hygienic panel and barrier sheet are flexible and tend to fold as an incontinent shifts his body position thereon. The hygienic product further comprises a flat stiffener sheet disposed between the hygienic panel and the barrier sheet. The stiffener sheet is characterized by a resilient characteristic tending to maintain it in a flat condition, thereby minimizing the tendency of the product to fold. The stiffener sheet is further characterized by having sufficient flexibility to avoid uncomfortable pressure concentrations on the person of the incontinent.

Other features relating to this aspect of the invention include a barrier sheet compositely formed by a urethane film and a fabric layer secured thereto and forming the lower surface of the pad. Preferably the this fabric is brushed to increase its coefficient of friction and, thus, further resist the tendency of the pad to fold.

The stiffener sheet may, advantageously, be quilted to the hygienic panel, which may be characterized, as above described. Advantages are also found in bonding the stiffener sheet to the barrier sheet.

The stiffener sheet is preferably formed of a nonwoven fabric, advantageously comprising polyester fibers.

Other objects of the invention are attained by a diaper which comprises a hygienic panel formed of fabric, as above characterized.

Additional features of the invention are found in a diaper configuration having a generally Y-shaped configuration, the specifics of which are described in detail.

Further ends of the invention are attained by a garment, fastening means therefor comprising a first piece of loop material secured to one portion of the garment, a flap of hook material secured to another portion of the garment and adapted to engage said first piece of loop material in fastening the garment and a second piece loop material, adapted to be engaged by flap when the garment is washed. The second piece of loop material has an outline greater than the outline of the flap. The flap is secured to the second piece of loop material by a line of stitching adjacent one end thereof. The second piece has marginal portions projecting outwardly from the flap and is secured to the garment by stitching extending through said projecting marginal portions.

A further aspect of the invention is found in a method for managing urine incontinence through the use of a hydrophilic/hydrophobic, as above characterized.

The above and other related objects and features of the invention will be apparent from a reading of the following description of preferred embodiments thereof, with reference to the accompanying drawings, and the novelty of the invention pointed out in the appended claims.

IN THE DRAWINGS

FIG. 1 is a plan view of one exemplary embodiment of the liquid-absorbing, incontinent pad of this invention, with the central portions thereof broken away;

FIG. 2 is an enlarged cross-sectional view, taken essentially on line 2—2 in FOG. 1;

FIG. 3 is a schematic cross-sectional view particularly illustrating the component portions comprising the integral single layer which defines the liquid absorbing means of the pad of FIG. 1;

FIG. 4 is a fragmentary isometric view presented to show the overall stacked arrangement of the liquid impervious layer and its components and the single layer of knitted cloth, which defines the two layer construction of the incontinent pad of this invention;

FIG. 5 is a perspective view of another incontinent pad embodiment of the present invention, with portions broken away;

FIG. 6 is an exploded, fragmentary, perspective view, of the pad seen in FIG. 5, illustrating the component layers thereof;

FIG. 7 is a section, on a greatly enlarged scale, taken on line 7—7 in FIG. 5;

FIG. 10 is a diagrammatic illustration, in cross section and in perspective, of the dispersion of urine in a hygienic panel fabric;

FIG. 11 is a perspective, exploded view of elements of the present diaper embodiment of the FIG. 12 is a perspective view of the elements of FIG. 11 in their assembled relation as a diaper construction;

FIG. 13 is a section, on an enlarged scale, taken on line 13—13 in FIG. 12;

FIG. 14 is a section, on an enlarged scale, taken on line 14—14 in FIG. 12;

FIG. 15 is a section, on an enlarged scale, taken on line 15—15 in FIG. 12;

FIG. 16 is a top view of the diaper construction of FIG. 12 as it would be folded and secured to embrace the crotch of a user;

FIG. 17 is a front view of the folded diaper construction;

FIG. 18 is a perspective view of an alternate embodiment of the invention comprising a separate, hygienic diaper liner; and FIG. 19 is a perspective view of an alternate embodiment of the invention comprising a diaper cover.

Figure 8:
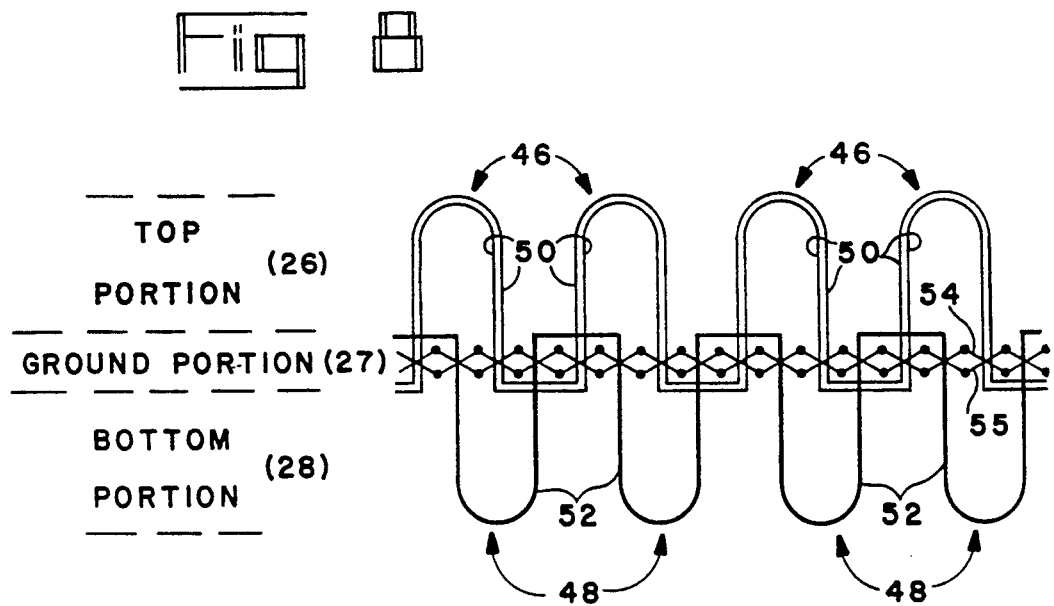
FIG. 8 is a greatly enlarged, schematic view illustrated the yarns comprising the knitted terry cloth, hygienic fabric of the present invention.
Figure 9:
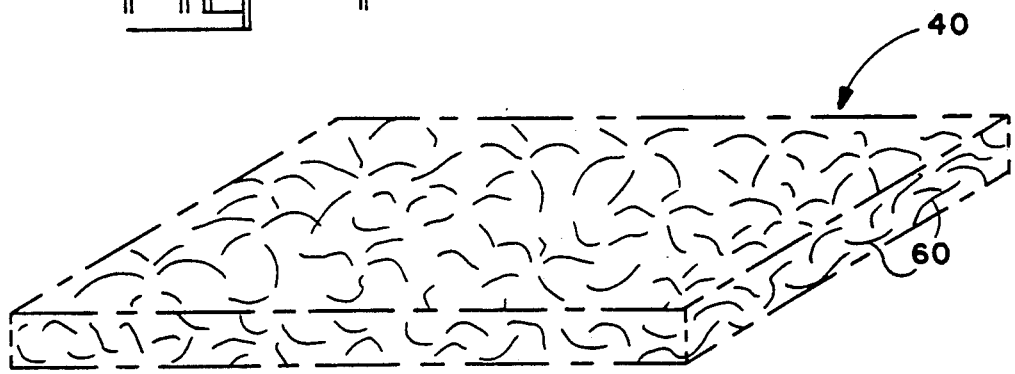
FIG. 9 is a perspective, on a greatly enlarged scale of a portion of a stiffener sheet employed herein.

In accordance with certain aspects of this invention, various features are illustrated and described as being particularly adapted to provide a liquid-absorbing pad usable as a bed pad, chair pad, wheelchair pad, diaper, and the like, generally referenced as hygienic products, known as such in this art. It is to be understood that the various features of this invention can be utilized singly or in various combinations thereof to provide a liquid-absorbing pad, usable with other liquids and in other applications, as desired.

Therefore, this invention is not to be limited to only the embodiments illustrated in the drawings because the drawings are merely utilized to illustrate exemplary ones of the wide variety of uses of the invention.

FIGS. 1–4

Reference is now made to FIG. 1 of the drawings, which illustrates one exemplary embodiment of the incontinent pad of this invention, being generally designated by reference numeral 20. The incontinent pad 20 is particularly adapted, dependent on the size and configuration selected, for use as a bed pad, chair pad, wheelchair pad, diaper, or the like, and, which pad is particularly adapted for use with, or by, a patient having urinary incontinence, or anyone subject to the drainage of body fluids.

As seen in FIGS. 1 and 2 of the drawings, the pad has a peripheral outline 21 and comprises a liquid impervious layer designated, generally by the reference numeral 22, also referenced herein as a "barrier sheet". The liquid impervious layer has opposed surfaces consisting of an inside surface 23 and an outside surface 24, being the exterior surface of the pad. The pad 20 has an absorbing means 25, also referenced herein as a "hygienic panel", attached to the layer 22 against one of the opposed surfaces and, in particular, against the inside surface 23.

In accordance with the teachings of this invention, the liquid-absorbing means or layer 25 consists of a single layer of knitted cloth and, as shown schematically in FIG. 3 of the drawings, such single layer of knitted cloth has an exposed front or top portion 26, a central, ground or base portion 27 and a back portion 28, which is also referenced herein as a "bottom portion". In one example of the invention, the single layer 25 is formed of knitted terry cloth. As is known in the knitted terry cloth art, the central ground 27 serves to hold the front and back portions 26 and 28 respectively together, while providing an integral structural separation therebetween. The known teachings of the prior art relating to this type of knitted, piled fabric are described in further detail below.

It will be pointed out that the term "knitted terry cloth" is used in the broad sense that the front portion 26 and bottom portion 28 comprise yarns in a loop, or loop-like, construction, which predominately characterizes the top and bottom portions of the panel 25.

Referring again to FIG. 1 of the drawings, the pad 20 preferably has rounded corners and also preferably has a tape 31, which protects the peripheral edges of its layers 22 and 25, holds layers 22 and 25 together and defines the peripheral outline 21 of such pad. The tape 31 may be any suitable tape known in the art and may be made of any suitable material. Preferably, the tape 31 is made of 100% polyester and is in the form of a so-called bias binding tape, which is fastened in position by suitable stitch means or stitches 32 as shown in FIG. 2 of the drawings.

The techniques used to define the rounded corners of the pad 20 and the manner of attaching the tape 31 at such corners is well known in the art. Once the tape 31 is stitched in position, the pad 20 has a compressed peripheral portion defined by an outer portion 33, which has an arcuate configuration as shown at 34. It will also be appreciated that the 100% polyester binding tape 31 can e a twilled or twill tape or may be made of any other suitable material and made by any other suitable weaving process.

The layers 22 and 25 may also be held together by so-called overcast stitching, or the like.

The single layer of knitted cloth 25 may be made entirely of a particular material and in one exemplary embodiment of this invention such particular material is in the form of a polyester. The polyester consists of a single variety of polyester or may consist of a plurality of varieties of polyester, as will be described subsequently.

The single layer of knitted cloth may also be made of a plurality of materials and the plurality of materials may consist of various combinations of polyester, cotton, rayon, nylon, and the like. Preferably such plurality of materials consists of two materials. In another exemplary embodiment of this invention, the plurality of materials consists of two materials, namely polyester and cotton. In this case, the front portion 26, of such single layer is made of 100% polyester and the back portion 28 is made of 100% cotton.

In a single layer made of polyester and cotton and when also considering the central base 27 of the single layer 25, the entire single layer may comprise between 25% and 62% cotton and between 75% and 38% polyester, respectively.

The front or top portion 26 of the single layer of the knitted terry cloth 25 is preferably made entirely (i.e. 100%) of polyester. Polyester is the preferred material for the top portion 26 even where other portions of the single layer 25 are formed of different materials. In addition, the ground or central base portion 27 may also be made entirely (i.e. 100%) of polyester or a combination of polyester and cotton or of 100% cotton. The combination of polyester and cotton of portion 27 may be a blend of 50% cotton and 50% polyester.

However, regardless of whether the single layer 25 is made entirely of a single material, such as polyester or a plurality of materials, such as polyester and cotton, the weight of the overall layer 25 may range from roughly 7 to 14 ounces per square yard.

It will also be appreciated that the single layer 25 may be made such that the front portion 26 is made of 100% polyester and the back portion is made of a blend of polyester and cotton. It will be appreciated that, in accordance with techniques known in the art, the quantity of fibers making up such blend of polyester and cotton may vary. In one embodiment of this invention a preferred blend of 50% polyester and 50% cotton is employed.

Another characteristic of the improved pad of this invention is that the single layer of knitted cloth is made such that the front portion 26 thereof consists entirely of uncut loops of material, which provide a wicking action from the outermost, or upper, surface 35 of the top portion 26 inwardly toward the back portion 28 of the layer 25. The uncut loops of material are preferably brushed loops.

The back portion 28 of the single layer 25 is made of a hydrophilic material which has a greater capacity to retain liquids as contrasted to the construction of the hydrophobic material defining the front portion 26, which provides the improved wicking action. While the material defining the back portion 28 may be the same basic material as the material of the front portion 26, where that material has been suitably modified to provide greater absorbency, or hydrophilicity, in one preferred embodiment of this invention, the material for the back portion is looped, uncut and unbrushed cotton.

Having thus described the construction of the pad 20, the detailed description will now proceed with a description of more details of the two component layers 22 and 25 which define the pad 20. In particular, the liquid impervious layer or barrier sheet 22 is preferably a sheet capable of withstanding hydrostatic water pressure of 100 pounds per square inch gauge (psig) without allowing passage of water therethrough. However, it will be appreciated that the particular layer 22 may be constructed so that it can withstand any desired hydrostatic water pressure which may be more or less than 100 psig, as desired.

The layer or sheet 22 is preferably comprised of a polymeric sheet 36 and may be comprised of either a knitted or a woven fabric 37 on which the polymeric sheet portion is laminated or coated. This may be achieved by extruding a polymeric material directly against the fabric 37, suitably forming the polymeric sheet portion 36, using suitable calendar rolls, or the like, all as is well known in the art. The polymeric sheet portion 36 may also be suitably coated onto the fabric 37 by any suitable means known in the art. The polymeric sheet portion 36 may also be laminated on to the fabric 37 using additional adhesive means, or the like, therebetween. The layer or sheet 22 is available from a number of manufactures.

The single layer 25 is capable of being produced by various manufacturers, however, one manufacturer is Guilford Mills of Greensboro, N.C. A typical manufacturer of layer 25 will have equipment (which is known in the art) capable of producing knitted terry cloth.

It will be appreciated that the various materials selected to define the layers 22 and 25 should be compatible with the liquids which are to be absorbed by the pad 20. In applications where the pad is for a person having urinary incontinence, or for the purpose of absorbing urine, the constituents of the pad are such that urine will not cause degradation or damage to the layers 22 and 25. The same principle applies to the other embodiments herein, as well as where the pad is particularly adapted to be used with other liquids. It will also be appreciated that the thread defining the stitches or stitch means 32, as well as the stitching means in the other embodiments herein, may be any suitable thread compatible with the liquids to be absorbed by the pad 20 and preferably such thread is made of polyester for a pad likely to wick or absorb urine.

The single layer of knitted terry cloth 25 may have an antimicrobial finish, if desired. The antimicrobial finish, if used, assures that the number of microorganisms will be reduced upon continued contact with such finish.

If desired, the pad 20, more specifically the yarns forming the back portion 28, may have a hydrophilic finish used thereon, when the back portion is formed of polyester yarns. If used, any suitable hydrophilic finish known in the art may be used; and, an exemplary finish, which may be used, is sold under the trade name "LR Finish" by Lubach International Consultants of Charlotte, N.C.

Similarly, any suitable, nonleaching antimicrobial finish known in the art may be used. The antimicrobial finish should be compatible with the hydrophilic finish. The antimicrobial finish is useful in killing a wide variety of bacteria, controls fermentation of urine, controls production of ammonia and controls the production of odor.

As previously mentioned, the layer 25 is in the form of a single layer of knitted cloth, such as terry cloth. This is in contrast to woven terry cloth and the knitted terry cloth may be made on various machines, known in the textile industry, utilizing a plurality of bars. The techniques or process employed to make the knitted single layer terry cloth is not a part of this invention, nor is the machine employed to make such cloth a part of this invention, inasmuch as any suitable technique or machine known in the textile art may be employed, as indicated previously.

It will also be appreciated that, as indicated earlier, various materials and various percentages of such materials may comprise the layer 25, which comprises the pad 20 of the invention. Materials and percentages for such layer may be as shown in the following chart. As indicated previously, the overall weight of the layer 25 may range from 7 to 14 ounces per square yard, with preferred weights being shown on such chart.

| MATERIALS AND PERCENTAGES FOR LAYER 25 OF PAD 20 | | |
| --- | --- | --- |
| CONTENT | OZ./ YD.² | FIBER CONTENT OF ENTIRE FABRIC |
| 100% Polyester Front 100% Cotton Back | 12.6 | 54 Cotton/46 Polyester |
| 100% Polyester Front 100% Cotton Back | 10.6 | 54 Cotton/46 Polyester |
| 100% Polyester Front 100% Cotton Back | 8.5 | 51 Cotton/46 Polyester |
| 100% Polyester Front 50% Polyester/50% Cotton Back | 12.6 | 25 Cotton/76 Polyester |
| 100% Polyester Front 50% polyester/50% Cotton Back | 10.5 | 26 Cotton/75 Polyester |
| 100% Polyester Front 50% Polyester/50% Cotton Back | 8.5 | 25 Cotton/75 Polyester |
| 100% Polyester Front "Great Feelings" Polyester Back | 12.5 | 53 "Great Feelings" Polyester/ 47 Polyester |
| 100% Polyester Front "Great Feelings" Polyester Back | 10.5 | 53 "Great Feelings" Polyester/ 47 polyester |
| 100% Polyester Front "Great Feelings" Polyester Back | 8.5 | 53 "Great Feelings" Polyester/ 47 Polyester |

It will also be noted that reference is made to a particular variety of polyester referred to as a so-called "Great Feelings" polyester and such "Great Feelings" polyester is a special polyester which is available from E. I. duPont de Nemours and Company of Wilmington, Del., and sold under the trade designation "Great Feelings". "Great Feelings" polyester consists of a 50/50 blend of 1.2 denier per filament and 2.0 denier per filament for an average of approximately 1.5 denier per filament. "Great Feelings" polyester is specifically designed for use in knit structures and contains an added whitener, which gives it a blue-white appearance. "Great Feelings" polyester differs from regular polyester in its blend of denier per filaments in the same yarn, whereby more spaces are created within such yarn, resulting in an improved capacity to retain liquid.

Thus, it is seen from the above description, that this invention provides a new liquid-absorbing pad, which provides optimum comfort and hygiene to a person coming into contact therewith.

The pad 20 of this invention is such that once liquid is introduced on the upper surface 35 of top portion 26, it passes through the central ground or base portion 27 and is retained in the back portion 28 and further that such liquid does not pass back through or return from the back portion 28 to the top portion 26.

As mentioned earlier in this specification, the term "liquid-absorbing" as used to define the new pad of this invention has a meaning now to be further explained. In particular, in the pad 20, liquid comes in contact with the top synthetic surface 35 (i.e. top portion 26) of the fabric 25, it passes through the interstices between the synthetic yarns. Because the liquid does not actually absorb into the fibers themselves, it wicks along the fibers. This is to say that the top portion 26 is hydrophobic. Gravity continues to pull the liquid down until it comes in contact with the intermediate layer or base portion 27 and bottom hydrophilic layer or back portion 28. As liquid comes in contact with these two layers 27-28, it begins to be dispersed into the yarns either by adsorption or absorption. It is held in this reservoir pulling it away from the top surface 35 of the knitted terry cloth layer 25, leaving the top surface 35 dry in a very short amount of time. The urine then remains in the absorbent layer "bottom" (i.e. back portion 28) until it is removed by laundering.

It is to be noted that all of the materials, above described and discussed, are capable of being washed and dried, using commercial laundering procedures, a substantial number of times without losing their structural integrity, or their hydrophobic/hydrophilic properties which contribute to the improved management of urine.

FIGS. 5-10

For various reasons, including patient comfort and ease of handling, it is desirable that incontinent pads by both light weight and highly flexible. The previously described pad 20 goes a long way toward achieving those ends.

It has been recognized that patient comfort can be further improved through the use of a urethane layer as the liquid impermeable component of the protective barrier sheet. The properties of urethane have been recognized as uniquely providing a greater flexibility for the pad, which is directly related to patient comfort. The use of a urethane layer provides other advantages discussed below.

Light weight, highly flexible incontinent pads, as provided by the present invention, while highly effective in the management of urine waste, under some conditions, do not have the drawback of "bunching up". That is, when used by a bed ridden incontinent, the pad has a tendency to fold upon itself when the incontinent shifts his position on the bed. Also, there is some tendency for the hygienic panel to separately fold upon itself when the incontinent shifts his position. In either event, a fold, so created, is uncomfortable to the user, and, can decrease the effective area of the pad so that its protective function is defeated.

The high degree of flexibility of urethane increases the tendency of the present incontinent pads to "bunch up", when that material is used as the impermeable member of a barrier sheet.

The incontinent pad 20', FIG. 5, now to be described, minimizes the tendency to "bunch up" and thus facilitates the use of urethane as a barrier material to enhance the comfort of an incontinent. Additional it will be pointed out that urethane films, employed for this purpose are more durable than other films, or sheets, of vinyl and butyl, which are more conventionally employed. Further a urethane film can be considerably thinner than corresponding films, or sheets of these more conventional materials. The end product, i.e., the incontinent pad will thus be lighter and have a reduced bulk, all of which results in various economies, such as a reduction in required storage space and reduced costs of laundering.

The incontinent pad 20' may comprise the same hygienic panel 25, as described in connection with the first embodiment. The pad 20' also comprises a barrier sheet 22', which serves the same functions described in connection with the liquid impervious layer, or barrier sheet, 22 of the first embodiment.

One of the improvements of this embodiment is found in the provision of a stiffener sheet 40, which resists folding of the pad 20'. The characteristics of the stiffener sheet are more fully set forth below.

The layers 25, 40 and 22' may have identical outlines, with their peripheral edges being secured by conventional overcasting stitching 42, as indicated in FIG. 5. The barrier sheet 22' comprises a urethane layer, or film, 36' and a fabric layer 37' bonded thereto. The hygienic panel 25 is secured to the stiffener sheet 40 by quilted stitching 44 to for a subassembly, the stiffener sheet may then be bonded to the urethane layer 36', and the latter may then be bonded to the fabric layer 37', all of which is more fully illustrated in FIGS. 6 and 7.

While the foregoing describes the preferred manner for incorporation into an incontinent pad, it is to be appreciated that variations may be made therefrom. For example, and not by way of limitation, the stiffener sheet 40 need not necessarily be bonded to the urethane film 36'. Likewise, the stiffener sheet 40 can find utility where the film, or sheet 36', is formed of a polymeric material other than urethane.

As indicated, the hygienic panel 25 of the pad 20' may be identical, in construction, with the hygienic panel of the pad 20. Thus, the panel 25 comprises a top portion 26, a central base, or ground portion 27 and a bottom portion 28. FIG. 7 shows these portions is greater detail, illustrating, loops 48 forming the top portion 26 and loops 48 forming the back portion 28, such loops having been previously referenced, and now illustrated in further detail for a more ready appreciation of the inventive concepts herein.

As previously indicated the panel 25 comprises a knit terry construction fabric. More specifically, this construction is a warp knit fabric, which is diagrammatically illustrated in FIG. 8. The inner ends of loops 46, formed by yarns 50, are intermeshed with the ground portion 27. Similarly, the inner ends of loops 48, formed by yarns 52, are intermeshed with the ground portion 27. The ground portion 27 further comprises at least one ground yarn 54, and, optionally, may include a second ground yarn 55.

The yarns 50, forming the top loops 46 are hydrophobic to provide the desired characteristic of enabling urine to wick therethrough, for eventual absorption into the bottom portion 28. It is further preferable that the yarns 50 be formed of continuous filament polymeric material which is hydrophobic, polyester being the preferred material. Additionally, it is preferred to employ a multi-filament, texturized polyester yarn.

The yarns 52, forming the bottom loops 48, are hydrophilic to provide the desired reservoir function for a void. The absorption capacity of the loops 48 is enhanced by employing yarns having a relatively large diameter, larger than and, preferably, at least twice that of the hydrophobic yarns 50. Yarns having a diameter of 6 by the cotton count have been found acceptable. Natural fiber staples are the preferred material for the hydrophilic yarns, with cotton yarns being preferred. However polymeric yarns having hydrophilic properties can also been employed. The "Great Feelings" yarns, above referenced, are representative of a hydrophilic, polymeric yarn. Also polyester yarns treated with a hydrophilic finish, such as the LR finish referenced above, are illustrative of another hydrophilic, polymeric yarn.

Where the ground portion 27 comprises both yarns 54 and 55, it is preferred that one of the ground yarns be polymeric for purposes of providing structural integrity and strength to the fabric panel, and that the other ground yarn be hydrophilic in order to facilitate wicking of urine through the ground layer and into the bottom, reservoir layer. Where the ground portion 27 comprises only one yarn, 54 or 55, its primary purpose is provide strength. Hydrophilic properties may also be provided by the use of a yarn also comprising cotton staples, as in a yarn comprising 50% polyester fibers and 50% cotton staples.

In use, the impingement of urine on the hygienic panel 25 is relative limited, i.e., it is concentrated on a relatively limited area of its top surface 35. The panel 25 is highly effective in limiting the spread of urine beyond this limited area of initial impingement.

This is a diagrammatically illustrated in FIG. 10, which shows a cross section through a section of a panel 25, taken through an area on which urine has impinged. The area of impingement is within the irregular outline, identified by reference character 56, on the top surface 35. Urine flow is indicated by arrows A. The urine passes downwardly, through the loops 46 of the top portion 26, with little or no lateral spread. The urine then passes through the central ground portion 27 into the bottom, reservoir portion 28. The urine then wicks, or migrates, laterally as it is absorbed into the loops 56, within a much larger area, indicated by reference character 58, on the bottom surface 50, of the panel 25.

It is to be noted that urine passes through the relatively dense, central ground portion 27 be being drawn into the absorbent yarn loops 48, assisted by the cotton content of the ground yarns 54. It is further to be noted that the density of the ground portion 27 prevents, or at least greatly minimizes, reverse flow of urine into the top portion 26, even when the panel is compressed by body pressures of the user. This is due to the absence of absorbent fibers in the top portion. This is to say, that passage of urine through the ground portion 27 is primarily a function of the presence of absorbent yarns, therebelow, which draw the water downwardly. Thus any flow of urine in a reverse direction would be the result of a physical force, such as compression. While this could occur, any urine so forced back into the top portion 26, would be quickly drawn back into the reservoir portion 28, by the absorbent action of the loops 48.

The net result is that the lateral area of the top surface 25 (in contacted with the user), which become wetted with urine is greatly minimized and thus the exposure of the user's skin to liquid urine is likewise limited. Further, exposure of the user's skin to urine in the area of direct impingement (outline 56), is minimized in that there is only a limited amount of urine which will be retained in the top portion 26. This small amount of urine will evaporate in a short period of time, thereby further minimizing the possibility of adverse affects from the user's contact with wet urine.

To summarize, the non-absorbent, hydrophilic, top layer 26 provides a wicking function and has sufficient mass, or structural integrity to space the ground portion 27, and more particularly, the urine containing bottom layer 28, from the person of the incontinent. The hydrophilic, bottom portion 28 provides a maximum absorption capacity.

Two fabric constructions have been found highly effective in providing these ends.

One preferred fabric has a weight of 10.5 ounces per square yard and is formed on a four bar, warp knitting machine. An exemplary method of forming such a fabric is taught in copending application Ser. No. 444,546, filed Nov. 30, 1989.

This 10.5 ounce fabric may correspond, essentially, to the fabric described in Example VI of said application. In the fabric so formed, the hydrophilic yarn 52, forming the loops 48, is 100% spun cotton having a denier of 886/1 (6 according to the cotton count system). The hydrophobic yarn 50, forming the loops 46, is texturized, polyester yarn having a denier of 168/68. It is to be noted that the loops 46 comprise two yarns 50, thus the effective denier of the yarns loops 50 is 336/136. A single yarn, having an equivalent denier could also be employed in forming the loops 46. One of ground yarns (54) is a spun 50% polyester/50% cotton yarn having a denier of 332/1 (16/1 by the cotton count) and the other ground yarn (55) is a multifilament, non-texturized polyester yarn having a denier of 70/32.

This 10.5 ounce fabric is further characterized in that the fabric comprises, on a weight percentage basis, 456.21% bottom loop yarn (52), 30.93% top loop yarn (50), 19.73% of one ground yarn (54) and 4.06% the other ground yarn (55).

This 10.5 ounce fabric has been found to have optimum absorption characteristics as well as providing a highly effective action in spacing the hydrophilic portion (28) from the incontinent. The 10.5 fabric is preferred for adult hygienic products, such as an incontinent pad intended for use by an adult incontinent.

The preferred fabric has a wight of 7.5 ounces per square yard and may be formed on a three bar, warp knitting machine. An exemplary method of forming such a fabric is also taught in said copending application Ser. No. 444,546.

In the 7.5 fabric, the hydrophilic yarn 52, forming the loops 48, is 100% spun cotton having a denier of 226/1 (20 according to the cotton count system). The hydrophobic yarn 50, forming the loops 46, is the same as in the 10.5 ounce fabric and is texturized, polyester yarn having a denier of 168/68. It is to be noted that the loops 46 comprise two yarns 50, thus the effective denier of the yarn loops 50 is 336/136. A single yarn, having an equivalent denier could also be employed in forming the loops 46. A single ground yarn is a multifilament non-texturized (for high strength) polyester yarn having a denier of 70/34. The single ground yarn may be chain stitched to provide structural integrity for the fabric.

This 7.5 ounce fabric is further characterized in that the fabric comprises, on a weight percentage basis, 48.73% bottom loop yarn (52), 44.76% top loop yarn (50), and 6.51% ground yarn.

The 7.5 ounce fabric also uniquely provides a maximized absorption capacity. Further, it is of lighter weight and bulk, and is, relatively flexible. For these reasons, the 7.5 ounce material is preferred for infant hygienic products, but its use is not so limited.

It is to be noted that three or four bar, warp knitting machines do not necessarily form loops in the classical sense schematically illustrated in FIGS. 7 and 8. This is to say that the term "loop", or "pile", as herein used, at least in the broad aspects of the present invention, is intended to designate a built up yarn construction, which predominately comprises one surface, or the other, of the fabric.

It is also to be noted that knitted fabrics are formed with a given number of wales per inch and courses per inch. To an extent, these parameters are a function of the particular knitting machine employed in forming the fabric, in any event, the selection of the number of wales per inch and courses per inch is within the ability of one skilled in the art to provide fabrics, as above characterized.

For the foregoing it is derived that preferred weight percentage of the hydrophilic portion of the fabric, i.e., the panel 25, approaches 50%. Further, weight of the hydrophobic portion of the fabric is, preferably, at least 30% of the fabric weight and, essentially, a constant, being in the order of 3.3 ounces per yard in a fabric weight range of approximately 7.5 ounces per yard and 10.5 ounces per yard.

A further point to note in connection with the hygienic panel 25 (whether formed of 7.5 to 10.5 ounce fabric) is the preferred brushing of the loops 46 of the top portion 26. The function served by providing brushed loops is to provide a greater comfort to the user, as well as to increase the interstices in the top surface and thereby increase the wicking function whereby urine migrates to the ground and bottom portions. Brushing, which is a known procedure, employing a rotary wire brush, breaks the continuous filaments of the yarns 50, which form the loops 46. This means that the top surface 35 is defined by filament ends, in addition to the curved filaments, which are not broken in the brushing process. Brushed surfaces have a very soft feel and minimize user discomfort.

It will also be noted that the preferred use of multifilament texturized yarn (i.e., yarn comprising continuous filaments the linear characteristics of which have been modified, as by crimping) further contributes to the creation of interstices and minimizing user discomfort.

One of the advantages of the knitted terry cloth of the present invention is that, because the loops 46 are anchored in the ground portion 27, it is capable of being brushed by conventional techniques to provide this comfort feature.

Brushing is not an accurate procedure in the sense that there is a measurable parameter to indicate the extent of which filaments or fracture, or filament ends are created. It is, nonetheless, an accepted measure in the industry to a fabric as being "lightly"brushed, "medium" brushed or "heavily" brushed to progressively indicate the brushing action.

The preferred degree of brushing is a "medium" brushed surface of the loops of the top portion 26. This provides a satisfactory comfort factor, without adversely affecting the urine wicking function of the top portion 26. This is to point out that it is undesirable for the top surface 35 to be defined by too great a number of filament ends. When the number of filaments ends increase, the spacing therebetween decreases. With the filament ends too closely spaced, the surface tension of the liquid urine will tend to cause the urine to "bead up" and rest upon the top surface 35, rather than passing down into and through the ground portion 27. Under appropriate circumstances, such a bead of urine could escape beyond the bounds of an incontinent pad and defeat the protective purpose for which it is provided.

Having completed a more detailed description of the panel 25, attention is next directed to FIG. 11 for an expanded description of the stiffener sheet 40. In its preferred form the stiffener sheet 40 is a non-woven fabric. Such non-woven fabrics are well known in the textile art. Basically non-woven fabrics comprise a plurality of randomly disposed, finite length fibers, or staples, 60 which are felted to form a unitary sheet. In order to minimize thickness, while providing a relatively high degree of structural integrity and strength, it is a common practice to embed these fibers in a resinous matrix.

The degree of stiffness, i.e., beam strength, of the sheet 40 is readily determinable from the following teachings.

The function of the stiffener sheet is to prevent, or minimize the tendency of the incontinent pad 20' from "bunching up" when in use. As above noted, incontinent pads have a tendency to move, relative to the bed, when a patient shifts his position. The pads will tend to fold upon themselves. This is not only uncomfortable to the user, but it, also decreases the effective area of protection provided by the pad, to the end that its protective function can be lost. The stiffener sheet 40 serves the function of maintaining the incontinent pad in a flat condition when in use.

The stiffener sheet is, however, by no means rigid, nor does it even approach a rigid condition. Rather, it is so flexible, that its presence in the pad 20' is essentially imperceptible to the patient user. Nonetheless, the stiffener sheet 40 possesses sufficient stiffness, and/or resilience, for it to maintain the pad 20' in a flat condition on a bed and resist the tendency of the pad to shift and fold upon itself to an uncomfortable "bunched up" condition.

Other considerations in the selection of the non-woven fabric of the stiffener sheet are weight, flexibility and washability. Desirably, the non-woven sheet should be light weight, an end which is usually attained by employing a relatively thin non-woven fabric.

The stiffener sheet also requires flexibility to prevent its being fractured during use and washing, as well as in the manufacturing process, as when being stitched.

The washability requirement is obvious from the stated purpose of the present invention to provide an improved, reusable hygienic product, which, inherently, requires washing.

It has been found that, for the incontinent pad 20', a stiffener sheet 40 comprising 100% polyester fibers, or staples, needle punched and heat set, with a thickness of approximately 3/63 inch and a weight of 4 ounces per square yard has been found satisfactory. Such non-woven fabrics are available from a number of commercial sources.

The effectiveness of the stiffener sheet is preventing "bunching" is preferably enhanced through the provision of the quilt stitching 44 which, in effect, secured the expanse of the hygienic panel 25 to the stiffener sheet 40.

The "bunching" problem is also minimized by further stiffening of the pad 20' through adhering the bottom surface of the stiffener sheet 40 to the upper surface of the barrier sheet 22'.

The barrier sheet 22' is compositely formed of a polymeric layer 36', preferably urethane, and a fabric layer 37'. In a preferred form, the polymeric layer 36' is a thin layer of urethane, preferably about 0.005 inches thick. The fabric layer 37' is preferably a light weight polyester tricot (a knit fabric).

The use of urethane for the layer 36' provides several advantages. These include the fact that it can provide the desired impermeability with an extremely thin thickness, and yet have the necessary durability to maintain its structural integrity over prolonged periods of use and repeated washing/drying cycles. Additionally, there is a minimal likelihood of the urethane layer 36' delaminating from the fabric 37'. Its flexibility enhances incontinent comfort. Further, being extremely thin, the urethane film reduces both the weight and bulk of the incontinent pad.

The fabric layer 37' is bonded to the lower surface of the polymeric layer 36' and the latter is bonded to the lower surface of the stiffener sheet 40, as indicated in FIG. 3. The method whereby such bonding is accomplished forms no part of the present invention. FIG. 6 does illustrate that the hygienic panel 25' and stiffener sheet are first secured together, as a subassembly, by the quilted stitching 44. The lower surface of this subassembly is then bonded to the polymeric layer 36' and fabric layer 37' bonded to the polymeric layer. The polymeric layer 36' and fabric layer 37' may be first bonded together as a subassembly, which is then bonded to the hygienic layer/stiffener sheet subassembly. Bonding may be accomplished by thermoplastic deformation of the polymeric layer, or through the use of adhesives, all as is known to those skilled in the art.

The provision of the stiffener sheet 40, attached to the panel 25', by quilted stitching (44) and the bonding of the urethane sheet 36' thereto all contribute to preventing the light weight incontinent pad 20' from "bunching up". To this end, it is also preferred to lightly bush the outer surface of the tricot fabric 37'. This increases the coefficient of friction of the lower surface 60 so that it will resist being shifted relative to the bed clothing.

It will be further noted, that bonding of the stiffener sheet of the polymeric layer can be omitted, as where materials, other than the preferred urethane material, are used.

In summary, the incontinent pads 20, 20' of the present invention provide a light weight, reusable incontinent pad, which provides a dry feel for incontinents and, for a given weight and bulk, is capable of absorbing a relatively large volume of urine.

FIGS. 11-17

Attention is next directed to FIGS. 11-17 for a description of a diaper embodiment of the present invention. This embodiment provides both a hygienic, reservoir function and a protective function. This is to say that, in use, when an incontinent voids, the urine is absorbed so that it is no longer a free liquid, and, further, the urine is contained so as to protect clothing or bedding from being soiled.

These functions are, respectively, provided by a hygienic panel, or liner, 120 and a barrier sheet 122 (FIG. 11), which are secured in assembled relation by a binding tape 124 (FIG. 12) to provide a compositely formed diaper, one-piece, construction, which is generally indicated by reference character 126 in FIG. 12.

The liner 120 and barrier sheet 122 both have the same configuration, or outline, which may be generally characterized as Y-shaped. When joined in assembled relation (FIG. 12), the Y-shaped liner and barrier sheet form a central front portion 128 and a back portion 130 having laterally projecting wings, or flaps, 132. This configuration has advantages in securing the diaper construction on the user, as will later appear.

The diaper construction 126 may further comprise a soaker panel 136 secured to the under surface of the hygienic panel 120 by stitching 138. The soaker panel 136 is of a lesser lateral extent than the panel 120 and barrier sheet 122, preferably being of a rectangular outline disposed centrally of the panel 120.

In its preferred form, the diaper 126 is secured on an incontinent by hook and loop fastening means, one form of which is well known and available under the trademark Velcro. Briefly, such means comprise a multi-element hook member which is engageable with a fibrous loop member. When engaged, the membrane resist separation forces in a direction parallel to their surfaces, and, yet, are readily separable by a force in a direction normal to their surfaces.

In the present diaper, a band of loop fabric 140 is secured to the barrier sheet 122, by stitching 142, FIG. 13. The band 140 is disposed at what becomes the outer surface of the upper end of the front portion 128, when the diaper is folded to embrace the crotch of an incontinent, as indicated in FIG. 17.

The "hook" portion of the fastening means comprises a pair of flaps 144, respectively secured to the inner surfaces of the wings 132. Each strip, preferably, is first secured to a loop piece 146 by a line of stitching 148, FIG. 11. The outline of each flaps is less than that of the loop piece 146 to which it is secured, so that marginal portions of the loop piece 146 project outwardly therefrom. This subassembly is then secured to the diaper by stitching 150 which extends through the projecting marginal portions of the loop piece 146, the liner 120 and the barrier sheet 122. This construction has the advantage of facilitating attachment of the hoop flaps 144 and loop pieces 146 by automated sewing machine techniques which reduce labor costs.

Other than when the diaper is being worn, the flaps 144 are engaged with the associated loop pieces 146. This feature is of particular importance when the diapers are washed in that the hooks of the flaps 144 are protected from being fouled with lint. Also the flap hooks are not free to engage and become tangled with other diapers. It is to be noted that the flaps 144 are formed of a resilient material which tends to automatically maintain them in engagement with their associated loop pieces 146.

When it is desired to put the diaper on an incontinent the flaps 144 are peeled from the loop pieces 146 and swung outwardly about the line of stitching 148, which functions as a hinge.

As indicated above, the panel 120 and barrier sheet 122 are held in assembled relation by the binding tape 124. More specifically, the binding tape 124 extends peripherally from one corner of the front diaper portion 128 along one side edge, along the back portion 130, and then along the other side edge, to the opposite corner of the front portion, at what becomes the upper edge of the diaper, when it is secured to an incontinent, FIG. 17. The binding tape is secured in place by stitching 152.

It is to be noted that the marginal edge portions of the diaper comprise only the panel 120 and barrier sheet 122, FIG. 14, except for the relatively limited span of the loop band 140, which is also embraced by the binding tape 124. This feature contributes to minimizing the bulk of the diaper, which is of particular significance, for an adult diaper, in making its use less apparent.

The preferred material for the binding tape 124 is a barrier material, which has the capability of preventing urine from leaking from the edge portions of the diaper. The same material used for the barrier sheet 122 may also be employed for the binding tape 124.

This type of material is relatively rigid and for that reason is not preferred in binding the upper edge of the front portion of the diaper, particular for infant diapers. This is in recognition of the fact that this upper edge is generally disposed in registered relation with the infant's navel button and can become a source of irritation, particularly in the case of new borns. Thus it is preferred that this upper edge be bound by a binding tape which is relatively soft. Thus, it will be seen that the upper edge of the front portion 128 is bound by a binding tape 154, which embraces the upper, front edge portions of the panel 120, barrier sheet 122 and loop band 140, and is secured by stitching 156, FIG. 13. The binding tape 154 extends beyond the side edges of the front portion 28 and then may be folded back, angled inwardly and bar tacked at 158 to form corner constructions which are highly durable in use. A suitable material for the binding tape 154 is a brushed polyester tricot, having a weight sufficient to provide structural integrity.

The binding tape 154 serves a further function in identifying the size of a given diaper.

As previously indicated, various sizes of diapers are required. These range from a very small size for premature infants to an extra large size for adults. The binding tape is, advantageously, color coded for size identification. For example, a pink tape may be used for the premature infant size, a blue tap may be used for a toddler size, a green tape for a small adult size and an orange tape for a medium adult size, etc.

It is a common practice to launder large numbers of diapers in a given washing load. The color coding thus provided facilitates sorting of the laundered diapers for reuse.

One of the features of the present invention is in providing a snug fit of the diaper on the incontinent, while accommodating a relatively wide range of body proportions with a given diaper size. In part, this end is attained through the provision of elasticized gathered sections 160 in the size edges of the diaper and a gathered section 162 in the upper edge of the back portion 130.

Gathered sections, as used herein, are, per se, well known. One such gathered section, illustrated in FIG. 15., comprises an elastic band 164 secured, at point G2, by stitching 166, within the binding tape 124. The stitching 166 is then extended to secure the liner 120 and barrier sheet 122 to the band 164, in gathered fashion, up to point G1. The binding tape 124 is also gathered between points G1 and G2.

The gathered section 162, in the back portion 130, may be formed in the same fashion as described in connection with the gathered sections 160 and preferably extends between the junction of the convexly curved wing portions, with the top of the back portion.

The end of obtaining a snug fit, for a wide range of body proportions is further attained by the configurational features now to be described.

Reference is next made to FIG. 11, from which it will be seen that the basic configuration of the diaper construction, as defined by the liner 120 and barrier sheet 122, is in the form of a rectangle having a width W and length L, characterized in that the length L is approximately twice the dimension of the width W. Further, the portions forming the wings, or flaps, 132, project outward a distance A outwardly of the basic rectangular configuration, the distance A being approximately 0.4 of the width W. Further, the point of maximum width of the wings 32 is spaced downwardly from the top of the back portion 30, a distance B which is approximately 0.1 of the length L.

The outer portion of each wing is convexly curved to the upper edge of the back portion 30 and then convexly curved, on a progressively increasing radius to a concavely curved portion which terminates, approximately, at the center of the length of the basic rectangular configuration of the diaper outline.

It has been found that this basic configuration can be proportionately scaled to provide basic diaper sizes suitable for premature infants, to the largest of adults.

Another factor in attaining a snug fit is found in the location of the gathered sections 160, 162. The gathered sections 160 extend from, approximately, the transition of the wing from a convex of a concave curvature, indicated by reference character G1 in FIG. 11, to a point adjacent and spaced beyond the juncture of that concave curvature with the basic rectangular configuration of the diaper, indicated by reference character G2. The gather section 162 extends across the full width W between the flaps 132, which are defined by the outwardly curved sections beyond the dimension W.

Yet another feature of the present invention, which contributes to the obtaining of a snug fit is found int he disposition of the hook and loop fasting means, i.e., the flaps 144 and the band 140. The loop band 140, preferably extends across the full width of the front portion 128. The hook flaps 144 are disposed generally centrally of and adjacent the outer ends of the wings 132. The flaps 144 are then angled downwardly from the top of the back portion 130 at an angle of approximately 15 deg. and extend inwardly from the hinge line, provided by stitching 148, which is normal thereto.

It is to be recognized that there is a tension force on the wing portions 132, when the flap 144 are engaged with the loop panel 140. In part, this tension force is the result of elongating the gathered, elasticized portions 160 and 162 to obtain a snug fit. The angled relationship of the flaps 144 minimizes twisting forces on the flaps 56, which might result in their inadvertent disengagement from the loop panel 140.

To complete the description of the diaper construction 126, the steps of its manufacture are preferably as follows. A first subassembly comprises the liner 120 and the soaker panel 136, attached thereto by the stitching 138. A second subassembly comprises the barrier sheet 122 and the loop panel 140, which is secured thereto by the stitching 142. These two subassemblies are superposed and initially joined by the stitching 166 employed in forming the elasticized, gathered portions 160 and 162. The binding tape 124 may then be secured by the stitching 152. Next, the binding tape 154 may be attached by the stitching 156 and bar tack 158.

Next there are two subassemblies, each comprising a flap 144, which is secured to a loop piece 146 by the hinge-forming stitching 148. These subassemblies are secured to the upper surface of the liner 120, by the stitching 150, which extends through the marginal edge portions of the loop pieces 146 and the barrier sheet 122.

The thread for the several stitchings employed in the diaper construction would preferably be resistant to degrading by urine or feces. Polyester thread is suitable for this purpose. The weight of thread can be readily ascertained by one skilled in the art for the purposes herein described.

The fully assembled diaper construction is illustrated in FIG. 12. It will be seen that the described construction, has a cup shape which facilitates its attachment to a user.

In use, the top edge of the back portion 130 is generally aligned with the incontinent's waist, at his backside. The front panel 128 may then be folded between the incontinent's legs and held against his stomach. The wings 132 are readily grasped to fold them in overlying relation with the front portion 128. The flaps 144 are freed from the loop pieces 146 and are pressed against the loop panel 140 to secure the diaper in place, with the elasticized portions 160 defining the leg openings for the incontinent. The diaper 126, in this fastened relation, is illustrated in FIGS. 16 and 17. It will be appreciated that the crotch portion would be folded upon itself, when the diaper is secured in place.

The provision of hook and loop fastening means facilitates adjustment of the wings 132 to the front portion 128. The disposition of the flaps 144 and the elasticized, gathered portions 160 and 162 cooperate to provide a snug fit, as the flaps 144 can be engaged with and attached to any portion of the loop panel 46 and the angled relation to the tabs orients the securing forces, relative thereto so that they are generally aligned with the elasticized portions 56 and 70. These portions are thus resiliently elongated to defining leg openings which snugly engage the infant's legs, without undue pressure thereon.

In accordance with one feature of the invention, the liner 120 comprises a single fabric piece (to which a soaker panel may be attached). It is further preferred that this single fabric piece provide both a wicking function and reservoir function for the same reasons, discussed above in connection with the incontinent pads 20, 20'. These ends are preferably attained by using the same fabrics, as used in the hygienic panel 25 and reference is made thereto for a description thereof.

The above referenced, warp knit terry cloth fabric having polyester yarn loops forming the top hydrophobic portion of the fabric and cotton yarn loops forming the bottom hydrophilic portion of the fabric, is preferred material for the liner 120. The user of such fabric is schematically illustrated in FIG. 14, where the top portion is identified by reference character 168, the ground portion is identified by reference character 170 and the bottom portion is identified by reference character 172. The top hydrophobic portion 168 defines the upper surface of the diaper, which engages the body of the incontinent, with the hydrophilic bottom portion 172 spaced therefrom by the ground portion 170.

It is further preferred that the referenced example of this fabric, which has a weight of 7.5 ounces per square yard is especially suitable for infant diapers.

For adult diapers, the 10.5 ounce fabric is preferred. The increased absorption capacity of this heavier fabric better suits the needs of providing a reservoir function for the larger voids of adults. Further, the increased mass of polyester yarns provides an greater cushioning effect. This is to say that the relatively larger weight of an adult is supported by this increased polyester yarn content to the end that squeezing of urine from the lower reservoir portion, back to the hydrophobic yarn portion, is minimized.

The barrier sheet 122 is, preferably, compositely formed by an impermeable, polymeric sheet, or film, 174 and a fabric layer 176, which is bonded thereto, as is indicated in FIG. 14. The lower surface of the fabric layer 176 defines the exterior surface of the diaper 126. The barrier sheet 122 may have the same characteristics as the barrier sheet 22 or 22' of the above described incontinent pads. However, in the case of a diaper construction, is preferred that the exterior surface, as defined by the fabric layer 176, have a low coefficient of friction. Thus the fabric would be unbrushed and preferably formed of polyester to provide a surface which enables clothing to readily move relative to the diaper. It is also preferred that the fabric layer 176 be a knit fabric, which inherently has a stretchable characteristic, as does the polymeric film 174. The barrier sheet 122 thus has a stretchable characteristic, which facilitates securing of the diaper on an incontinent.

It is to be noted that the components of the diaper construction are capable of being repeatedly washed, without loss of their functional characteristics.

In connection with washing, two factors will be noted with respect to the preferred fabric forming the liner 120. Because this fabric employs cotton yarns and/or cotton/polyester yarns, it will shrink, when washed. Further, because the fabric is warp knitted, the shrinkage factor will be directional. This is to say that there will be a greater percent shrinkage in its warp direction, than in a direction normal thereto.

This leads to the preferred orientation of the warp yarns normal to the length dimension (L) of the liner. Further, in cutting the liner 120, it is cut oversize, proportionate to its shrinkage factors, so that it will more precisely match the outline of the barrier sheet 122 (which does not shrink) after the first few washings of the diaper.

FIGS. 18 and 19

Certain aspect of the present invention are also applicable to diaper liners and diaper covers which are used as separate elements.

A separate diaper liner 178 is illustrated in FIG. 18. It may comprise the same hygienic panel 120, described in connection with the diaper connection 126, as seen in FIG. 11. Likewise a soaker panel 136 may be secured to the undersurface thereof by stitching 138. This separate liner then comprises a backing panel 180 having the same outline as the liner 20. The backing panel may be any light weight, washable fabric. A polyester tricot fabric is suitable as a backing panel. The marginal edge portions of the liner 120 and the backing panel 180 are secured together by overcast stitching 182.

The same hook and loop fastening means, as employed as in the prior embodiment, may also be used in securing the separate diaper liner 178 to an incontinent. Thus a loop panel 140 is secured to the lower surface of the backing panel 180 by stitching 184 and further secured by the overcast stitching 182. Likewise hook flaps 144 and loop pieces 146 are secured to the upper surface of the liner 20 in the wing areas (132) thereof.

The separate cover embodiment of the present invention is illustrated in FIG. 19 and identified by reference character 186 In simplest terms, the separate cover 186 is identical in construction with the diaper construction 126, excepting only that the liner 120 (and its attached soaker panel 136) has been omitted. Minor modifications may, of course, be made to accommodate the reduced thickness resulting from the omission of the liner element. Elements in the separate cover 186, which have been previously described, are identified by like reference characters. The barrier sheet 122 is formed of an impervious film and fabric layer, all as previously described. It is not believed that repetition of a detailed description of these elements, and there relationships is required.

The separate liner 178 may be used where it is desired to maintain maximum air circulation for the crotch area of the patient. This separate liner 178 may also be used in combination with the separate cover 186, where it is desired to provide protection against soiling of bed clothes or clothing. The use of these separate elements facilitates laundering. This is to say that, in many instances, the liner may require changing, but the cover is either unsoiled, or can be wiped clean by a cloth. The separate cover can be reused several times, before washing is required. Thus it is necessary to wash only the separate liners.

Variations in the described embodiments will occur to those skilled in the art within the spirit and scope of the present inventive concepts and shall be deemed within the purview of the following claims.

Having thus described the invention, what is claimed is novel and desired to be secured by Letters Patent of the United States is:

1. An integrally knit textile fabric for use in hygienic products,
    said fabric having separate hydrophobic and hydrophilic properties, and comprising
    a top portion formed by hydrophobic yarn piling, outer portions of the hydrophobic piling yarns defining the upper surface of the fabric,
    a bottom portion formed by hydrophilic yarn piling, outer portions of the hydrophilic piling yarns defining the lower surface of the fabric, and
    a central portion comprising inner end portions of the hydrophobic and hydrophilic piling yarns and ground yarn means interconnected with said piling yarns and providing dimensional stability for the fabric,
    said top portion being characterized in that said hydrophobic yarn piling wicks liquid from the upper surface of the fabric into the central portion and is incapable of retaining any substantial amount of liquid therein,
    said bottom portion being characterized in that said hydrophilic yarn piling wicks liquid from the central portion into the remainder of the yarn piling and provides a reservoir function in retaining the liquid, and
    further characterized in that
    the inner end portions of the hydrophobic and hydrophilic yarns and the ground yarn of the central portion are knitted together in overlapping juxtapositon with each other, and
    said central portion has a high density of yarns which facilitates dispersal of liquid from the top portion into the bottom portion and further provides a barrier inhibiting reverse flow of liquid therethrough, thereby minimizing passage of liquid from the bottom portion to the top portion as a result of pressures on the fabric, and
    the ground yarn means has a relatively high strength. whereby, the upper surface of the fabric has a dry feel shortly after liquid is discharged thereon.

2. An absorbent textile fabric adapted to provide a dry feel on one surface thereof,
    said fabric having separate hydrophobic and hydrophilic properties, and comprising
    a top portion of finite thickness, an outer portion of which defines the upper surface of the fabric,
    a bottom portion of finite thickness, an outer portion of which defines the lower surface of the fabric, and
    a central portion in which inner end portions of the top and bottom portions and ground yarn means interconnected therewith and providing dimensional stability for the fabric,
    said top portion being characterized that it comprises a piling formed by hydrophobic yarns, inner end portions of which extend into the central portion, said top portion being further characterized in that
said hydrophobic yarn piling wicks liquid from the
upper surface of the fabric into the central portion
and in incapable of retaining any substantial
amount of liquid therein, said bottom portion being characterized in that it
comprises a piling formed by hydrophilic yarns,
inner end portions of which extend into the central
portion, said bottom portion being further characterized in
that said hydrophilic yarn piling wicks liquid from
the central portion into the remainder of the yarn
piling and provides a reservoir function in retaining
the liquid, further characterized in that the hydrophobic yarn of the top portion essentially
consists of texturized yarn comprised of continuous
filaments of a polymeric material, and the ground yarn means has a relatively high strength,
whereby, the upper surface of the fabric has a dry feel
shortly after liquid is discharged thereon.

3. A textile fabric as in claim 2, which is an integrally knit construction, further characterized in that the inner end portions of the hydrophobic and hydrophilic yarns and the ground yarn of the central portion are knitted together in overlapping juxtaposition with each other, and said central portion has a high density of yarns which facilitates dispersal of liquid from the top portion into the bottom portion and further provides a barrier inhibiting reverse flow of liquid therethrough, thereby minimizing passage of liquid from the bottom portion to the top portion as a result of pressures on the fabric, and the ground yarn means comprises a yarn consisting of polymeric fiber staples and natural fiber staples.

4. A textile fabric as in claim 2, which is an integrally knit construction, further characterized in that the inner end portions of the hydrophobic and hydrophilic yarns and the ground yarn of the central portion are knitted together in overlapping juxtaposition with each other, and said central portion has a high density of yarns which facilitates dispersal of liquid from the top portion into the bottom portion and further provides a barrier inhibiting reverse flow of liquid therethrough, thereby minimizing passage of liquid from the bottom portion of the top portion as a result of pressures on the fabric, and the ground yarn means comprise
a first ground yarn formed of polymeric filaments and
a second ground yarn formed of both polymeric fibers and natural fiber staples.

5. A textile fabric as in claim 2 further characterized in that the top portion piling comprises uncut loops defining the top surface of the fabric, and
said top portion piling is brushed.

6. A textile fabric as in claim 5 further characterized in that the top portion piling is medium brushed to a degree insufficient for liquid to "bead up" on its surface as a result of the surface tension of liquid impinged thereon.

7. A textile fabric as in claim 2, which is an integrally knit construction, further characterized in that the inner ends of the hydrophobic and hydrophilic yarns and the ground yarn of the central portion are knitted together is overlapping juxtaposition with each other, and said central portion has a high density of yarns which facilitates dispersal of liquid from the top portion into the bottom portion and further provides a barrier inhibiting reverse flow of liquid therethrough, thereby minimizing passage of liquid from the bottom portion to the top portion as a result of pressures on the fabric, and the ground yarn means has a relatively high strength, and further characterized in that the weight of the fabric is between about 7 and 13.5 ounces per square yard.

8. A textile fabric as in claim 7 further characterized in that the weight of the fabric is approximately 7.5 ounces per square yard, the denier of the hydrophilic yarn is approximately 226/1, the denier of the hydrophobic yarn is approximately 336/136, the weight of the hydrophilic yarn is approximately 49% of the weight of the fabric, the weight of the hydrophobic yarn is approximately 45% of the weight of the fabric, and the balance of the weight of the fabric is comprised of the ground yarn means.

9. A textile fabric as in claim 8 further characterized in that the ground yarn means comprises multifilament polyester yarn having a denier of approximately 70/34.

10. A textile fabric as in claim 9 further characterized in that the fabric is a three bar, warp knit fabric.

11. A textile fabric as in claim 9 further characterized in that the hydrophobic yarn piling is formed by a pair of textured polyester yarns, each having a denier of approximately 168/68.

12. A textile fabric as in claim 7 further characterized in that the weight of the fabric is approximately 10.5 ounces per square yard, the denier of the hydrophilic yarn is approximately 886/1, the denier of the hydrophobic yarn is approximately 336/136, the weight of the hydrophilic yarn is approximately 45% of the weight of the fabric, the weight of the hydrophobic yarn is approximately 30% of the weight of the fabric, and the balance of the weight of the fabric is comprised of the ground yarn means.

13. A textile fabric as in claim 12 further characterized in that the ground yarn means comprises
a first multifilament, non-texturized polyester ground yarn having a denier of approximately 70/34, and
a second spun ground yarn comprising 50% cotton staples a 50% polyester fibers having a denier of 332/1.

14. A textile fabric as in claim 13 further characterized in that the second ground yarn comprises approximately 20% of the weight of the fabric.

15. A textile fabric as in claim 13 further characterized in that the fabric is a four bar, warp knit fabric.

16. A textile fabric as in claim 13 further characterized in that said top portion piling is brushed.

17. A textile fabric as in claim 13 further characterized in that the hydrophobic yarn piling is formed by a pair of textured polyester yarns, each having a denier of approximately 168/68.

18. An absorbent textile fabric adapted to provide a dry feel on one surface thereof, said fabric having separate hydrophobic and hydrophilic properties, and comprising a top portion formed by hydrophobic yarn piling, outer portions of the hydrophobic piling yarns defining the upper surface of the fabric, a bottom portion formed by hydrophilic yarn piling, outer portions of the hydrophilic piling yarns defining the lower surface of the fabric, and a central portion comprising inner end portions of the hydrophobic and hydrophilic piling yarns and ground yarn means interconnected with said piling yarns and providing dimensional stability for the fabric, said top portion being characterized in that said hydrophobic yarn piling wicks liquid from the upper surface of the fabric into the central portion and is incapable of retaining any substantial amount of liquid therein, said bottom portion being characterized in that said hydrophilic yarn piling wicks liquid from the central portion into the remainder of the yarn piling and provides a reservoir function in retaining the liquid, further characterized in that the bottom portion hydrophilic yarn piling approximates fifty percent of the fabric weight, the top portion hydrophobic yarn comprises at least 30% of the weight of the fabric and the balance of the fabric weight is formed by the ground yarn means, whereby, the upper surface of the fabric has a dry feel shortly after liquid is discharged thereon.

19. A textile fabric as in claim 18 further characterized in that the top portion, hydrophobic yarn weight is approximately 3.3 ounces per square yard.

20. A textile fabric as in claim 18 further characterized in that the weight of the fabric is between about 7 and 13.5 ounces per square yard.

21. A textile fabric as in claim 20 further characterized in that the hydrophobic yarn is a textured yarn comprising continuous polyester filaments, the hydrophilic yarn comprises spun cotton staples, the bottom portion hydrophilic yarn piling approximates fifty percent of the fabric weight, the top portion hydrophobic yarn comprises at least 30% of the weight of the fabric and the balance of the fabric weight is formed by the ground yarn means.

22. A textile fabric as in claim 21 further characterized in that the top portion, hydrophobic yarn weight is approximately 3.3 ounces per square yard.

23. A liquid absorbent incontinent pad adapted to be interposed between an incontinent and a generally flat supporting surface, said pad including a hygienic panel adapted to contact the person of an incontinent and absorb liquid discharged by the incontinent, a barrier sheet forming the lower exterior surface of said pad and adapted to contain liquid discharged by the user, and means for securing said hygienic panel and barrier sheet is superposed, assembled relation, characterized in that the hygienic panel is an integrally knit, piled fabric having separate hydrophobic and hydrophilic properties, and comprising a central ground portion, a top portion formed by hydrophobic yarn piling projecting upwardly from the central ground portion and defining the upper surface of said pad, and a bottom portion, formed by hydrophilic yarn piling projecting downwardly from said central portion and defining the lower surface of the fabric, said central portion comprising inner end portions of the hydrophilic and hydrophobic yarns and ground yarn means interconnected with said piling yarns and providing dimensional stability for the fabric, and further characterized in that the top piling portion has the capability of wicking liquid from the upper surface of said pad and the bottom piling portion has the capability of absorbing liquid and providing a reservoir function to minimize the liquid in the top piling portion and particularly the upper surface which is contacted by the incontinent, and the inner end portions of the hydrophobic and hydrophilic yarns and the ground yarn of the central portion are knitted together in overlapping juxtaposition with each other, and said central portion has a high density of yarns which facilitates dispersal of liquid from the top portion into the bottom portion and further provides a barrier inhibiting reverse flow of liquid therethrough, thereby minimizing passage of liquid from the bottom portion of the top portion as a result of pressures on the fabric, and the ground yarn means has a relatively high strength, whereby, the upper surface of the incontinent pad has a dry feel shortly after liquid is discharged thereon.

24. An absorbent pad as in claim 23 further characterized in that the lower surface of the bottom piling portion contacts and is supported by said barrier sheet.

25. A liquid absorbent incontinent pad adapted to be interposed between an incontinent and a generally flat supporting surface, said pad including a hygienic panel having an upper surface adapted to contact the person of an incontinent and absorb liquid discharged by the incontinent, a barrier sheet forming the lower exterior surface of said pad and adapted to contain liquid discharged by the user, and means for securing said hygienic panel and barrier sheet in superposed, assembled relation, characterized in that said hygienic panel has separate hydrophobic and hydrophilic properties, and comprises a fabric constructed with a top portion, of finite thickness, an outer portion of which defines the upper surface of the incontinent pad, a bottom portion of finite thickness, an outer portion of which defines the lower surface of the panel, and a central portion in which inner end portions of the top said bottom portion are intermeshed, said top portion being characterized in that it is formed of hydrophobic yarns, inner end portions of which extend into the central portion, said top portion being further characterized in that it is hydrophobic and wicks liquid from the upper surface of the fabric to the central portion and is incapable of retaining any substantial amount of liquid therein, said bottom portion being further characterized in that it is formed of hydrophilic yarns, inner end portions of which extend into said central portion, said bottom portion being further characterized in that it wicks liquid from the central portion into the remainder of the bottom portion and provides a reservoir function in retaining the liquid, further characterized in that the hydrophobic yarn of the top portion essentially consists of a texturized yarn comprised of continuous filaments of a polymeric material, and the ground yarn means has a relatively high strength, whereby, the upper surface of the incontinent pad has a dry feel shortly after liquid is discharged thereon.

26. An incontinent pad as in claim 25 wherein the hygienic panel is further characterized in that the inner end portions of the hydrophobic and hydrophilic yarns and the ground yarn of the central portion are knitted together in overlapping juxtaposition with each other, and said central portion has a high density of yarns which facilitates dispersal of liquid from the top portion into the bottom portion and further provides a barrier inhibiting reverse flow of liquid therethrough, thereby minimizing passage of liquid from the bottom portion to the top portion as a result of pressures on the hygienic panel, and the ground yarn means has a relatively high strength.

27. An incontinent pad as in claim 26 wherein the hygienic panel is further characterized in that the ground yarn means are comprise a yarn consisting polymeric fiber staples and natural fiber staples.

28. An incontinent pad as in claim 26 wherein the hygienic panel is further characterized in that the ground yarn means comprise a first ground yarn formed of polymeric filaments and a second ground yarn formed of both polymeric fibers and natural fiber staples.

29. An incontinent pad as in claim 26 further characterized in that the hygienic panel and barrier sheet are highly flexible and tend to fold as an incontinent shifts his body position thereon, said pad further comprising a flat stiffener sheet disposed between the hygienic panel and the barrier sheet, said stiffener sheet being characterized by a resilient characteristic tending to maintain it in a flat condition, thereby minimizing the tendency of the incontinent pad to fold, said stiffener sheet being further characterized by having sufficient flexibility to avoid uncomfortable pressure concentrations on the person of the incontinent.

30. An incontinent pad as in claim 29 further characterized in that the barrier sheet comprises an impervious sheet of polymeric material and a thin, flexible fabric bonded to the lower surface of the polymeric sheet and defining the exterior surface of the lower exterior surface of the pad, characterized in that the thin flexible fabric is brushed.

31. An incontinent pad as in claim 30 further characterized in that the impervious sheet of the barrier sheet is a thin film of urethane.

32. An incontinent pad as in claim 29 further characterized in that the stiffener sheet is secured to the panel sheet.

33. An incontinent pad as in claim 32 further characterized in that the stiffener sheet is secured to the hygienic panel by quilted stitching.

34. An incontinent pad as in claim 33 wherein the barrier sheet comprises an impervious sheet of polymeric material and a thin, flexible fabric bonded to the lower surface of the polymeric sheet and defining the exterior surface of the lower exterior surface of the pad, and further characterized in that the impervious sheet directly underlies the stiffener sheet and is bonded thereto.

35. An incontinent pad as in claim 34 further characterized in that the impervious sheet of the barrier sheet is a thin film of urethane, and the fabric of the barrier sheet is a knit polyester, which is brushed to increase its coefficient of friction.

36. An incontinent pad as in claim 35 further characterized in that the pad consists of said hygienic panel, said stiffener sheet and said barrier sheet, each having essentially the same outline, and disposed in registered relationship, and further characterized by overcast stitching securing the peripheral, marginal edge portions of said hygienic panel, said stiffener sheet and said barrier sheet.

37. An incontinent pad as in claim 29 further characterized in that the stiffener sheet is a non-woven fabric.

38. An incontinent pad as in claim 37 further characterized in that the stiffener sheet is a non-woven fabric comprising polymeric fibers.

39. An incontinent pad as in claim 38 further characterized in that the polymeric fibers are polyester fibers, the stiffener sheet has a thickness of approximately 3/64 inch and a weight of approximately 4 ounces per square yard, and the polyester fibers are needle punched and heat set.

40. An incontinent pad as in claim 39 further characterized in that the stiffener sheet is secured to the hygienic panel by quilted stitching, the barrier sheet comprises an impervious film of urethane, and a thin, flexible fabric bonded to the lower surface of the polymeric sheet and defining the exterior surface of the lower exterior surface of the pad, and further characterized in that the impervious sheet directly underlies the stiffener sheet and is bonded thereto, and the fabric of the barrier sheet is a knit polyester, which is brushed to increase its coefficient of friction.

41. An incontinent pad as in claim 25 wherein the hygienic panel is further characterized in that the top portion piling comprises uncut loops defining the top surface of the fabric, and said top portion piling is brushed.

42. An incontinent pad as in claim 41 wherein the hygienic panel is further characterized in that the top portion piling is medium brushed to a degree insufficient for liquid to "bead up" on its surface as a result of the surface tension of liquid impinged thereon.

43. An incontinent pad as in claim 25 wherein the hygienic panel is further characterized in that the bottom portion hydrophilic yarn piling approximates fifty percent of the fabric weight, the top portion hydrophobic yarn comprises at least 30% of the weight of the fabric and the balance of the fabric weight is formed by the ground yarn means.

44. An incontinent pad as in claim 43 wherein the hygienic panel is further characterized in that the top portion, hydrophobic yarn weight is approximately 3.3 ounces per square yard.

45. An incontinent pad as in claim 25 wherein the hygienic panel is further characterized in that the weight of the fabric is between about 7 and 13.5 ounces per square yard.

46. An incontinent pad as in claim 25 wherein the hygienic panel is further characterized in that the hydrophobic yarn is a textured yarn comprising continuous polyester filaments, the hydrophilic yarn comprises spun cotton staples, the bottom portion hydrophilic yarn piling approximately fifty percent of the fabric weight, the top portion hydrophobic yarn comprises at least 30% of the weight of the fabric and the balance of the fabric weight is formed by the ground yarn means.

47. An incontinent pad as in claim 46 wherein the hygienic panel is further characterized in that the top portion, hydrophobic yarn weight is approximately 3.3 ounces per square yard.

48. An incontinent pad as in claim 46 wherein the hygienic panel is further characterized in that the weight of the fabric is between about 7 and 13.5 ounces per square yard.

49. An incontinent pad as in claim 48 wherein the hygienic panel is further characterized in that the weight of the fabric is approximately 7.5 ounces per square yard, the denier of the hydrophilic yarn is approximately 226/1, the denier of the hydrophilic yarn is approximately 336/136, the weight of the hydrophilic yarn is approximately 49% of the weight of the fabric, the weight of the hydrophobic yarn is approximately 45% of the weight of the fabric, and the balance of the weight of the fabric is comprised of the ground yarn means.

50. An incontinent pad as in claim 49 wherein the hygienic panel is further characterized in that the ground yarn means comprises multifilament polyester yarn having a denier of approximately 70/34.

51. An incontinent pad as in claim 50 wherein the hygienic panel is further characterized in that the fabric is a three bar, warp knit fabric.

52. An incontinent pad as in claim 50 wherein the hygienic panel is further characterized in that the hydrophobic yarn piling is formed by a pair of textured polyester yarns, each having a denier of approximately 168/68.

53. An incontinent pad as in claim 48 wherein the hygienic panel is further characterized in that the weight of the fabric is approximately 10.5 ounces per square yard, the denier of the hydrophilic yarn is approximately 886/1, the denier of the hydrophobic yarn is approximately 336/136, the weight of the hydrophilic yarn is approximately 45% of the weight of the fabric, the weight of the hydrophobic yarn is approximately 30% of the weight of the fabric, and the balance of the weight of the fabric is comprised of the ground yarn means.

54. An incontinent pad as in claim 53 wherein the hygienic panel is further characterized in that the ground yarn means comprises a first multifilament, non-texturized polyester ground yarn having a denier of approximately 70/34, and a second spun ground yarn comprising 50% cotton staples and 50% polyester fibers having a denier of 332/1.

55. An incontinent pad as in claim 54 wherein the hygienic panel is further characterized in that the second ground yarn comprises approximately 20% of the weight of the fabric.

56. An incontinent pad as in claim 54 wherein the hygienic panel is further characterized in that the fabric is a four bar, warp knit fabric.

57. An incontinent pad as in claim 54 wherein the hygienic panel is further characterized in that said top portion piling is brushed.

58. A hygienic product in the form of an incontinent pad, comprising an absorbent hygienic panel, said panel having a large lateral extent relative to its thickness, and an underlying barrier sheet of approximately the same lateral extent, characterized in that the hygienic panel and barrier sheet are flexible and tend to fold as an incontinent shifts his body position thereon, said product further comprising a flat stiffener sheet disposed between the hygienic panel and the barrier sheet, said stiffener sheet being characterized by a resilient characteristic tending to maintain it in a flat condition, thereby minimizing the tendency of the product to fold, said stiffener sheet being further characterized by having sufficient flexibility to avoid uncomfortable pressure concentrations on the person of the incontinent.

59. An hygienic product as in claim 58 wherein the barrier sheet comprises an impervious sheet of polymeric material and a thin, flexible fabric bonded to the lower surface of the polymeric sheet and defining the exterior surface of the lower exterior surface of the product, characterized in that the thin flexible fabric is brushed.

60. An hygienic product as in claim 59 further characterized in that the impervious sheet of the barrier sheet is a thin film or urethane.

61. An hygienic product as in claim 58 further characterized in that the stiffener sheet is secured to the hygienic panel.

62. An hygienic product as in claim 61 further characterized in that the stiffener sheet is secured to the hygienic panel by quilted stitching.

63. An hygienic product as in claim 62 wherein the barrier sheet comprises an impervious sheet of polymeric material and a thin, flexible fabric bonded to the lower surface of the polymeric sheet and defining the exterior surface of the lower exterior surface of the product, and further characterized in that the impervious sheet directly underlies the stiffener sheet and is bonded thereto.

64. An hygienic product as in claim 63 further characterized in that the impervious sheet of the barrier sheet is a thin film of urethane, and the fabric of the barrier sheet is a knit polyester, which is brushed to increase its coefficient of friction.

65. A hygienic product as in claim 64 further characterized in that the product consists of said hygienic panel, said stiffener sheet and said barrier sheet, each having essentially the same outline, and disposed in registered relationship, and further characterized by overcast stitching securing the peripheral, marginal edge portions of said hygienic panel, said stiffener sheet and said barrier sheet.

66. An hygienic product as in claim 58 further characterized in that the stiffener sheet is a non-woven fabric.

67. An hygienic product as in claim 66 further characterized in that the stiffener sheet is a non-woven fabric comprising polymeric fibers.

68. An hygienic product as in claim 67 further characterized in that the polymeric fibers are polyester fibers, the stiffener sheet has a thickness of approximately 3/64 inch and a weight of approximately 4 ounces per square yard, and the polyester fibers are needle punched and heat set.

69. An hygienic product as in claim 68 further characterized in that the stiffener sheet is secured to the hygienic panel by quilted stitching, the barrier sheet comprises an impervious film of urethane, and a thin, flexible fabric bonded to the lower surface of the polymeric sheet and defining the exterior surface of the lower exterior surface of the product, and further characterized in that the impervious sheet directly underlies the stiffener sheet and is bonded thereto, and the fabric of the barrier sheet is a knit polyester, which is brushed to increase its coefficient of friction.

70. A diaper adapted to be worn by an incontinent in the fashion of a garment. said diaper including a hygienic panel forming the inner surface of the diaper and adapted to contact the person of an incontinent and absorb liquid discharged by the incontinent, a barrier sheet forming the outer, exterior surface of said pad and adapted to contain liquid discharged by the user, and means for securing said hygienic panel and barrier sheet in superposed, assembled relation, characterized in that the hygienic panel is an integrally knit, piled fabric having separate hydrophobic and hydrophilic properties and comprising a central ground portion, a top portion formed by hydrophobic yarn piling projecting upwardly from the central ground portion and defining the inner surface of said diaper, and a bottom portion, formed by hydrophilic yarn piling projecting downwardly from said central portion and defining the lower, outer surface of the fabric, said central portion comprising inner end portions of the hydrophilic and hydrophobic yarns and ground yarn means interconnected with said piling yarns and providing dimensional stability for the fabric, and further characterized in that the top piling portion has the capability of wicking liquid form the inner surface of said diaper, and the bottom piling portion has the capability of absorbing liquid and providing a reservoir function to minimize the liquid in the top piling portion and particularly the inner surface which is contacted by the incontinent, and the inner end portions of the hydrophobic and hydrophilic yarns and the ground yarn of the central portion are knitted together in overlapping juxtaposition with each other, and said central portion has a high density of yarns which facilitates dispersal of liquid from the top portion into the bottom portion and further provides a barrier inhibiting reverse flow of liquid therethrough thereby minimizing passage of liquid from the bottom portion of the top portion as a result of pressures on the fabric, and the ground yarn means has a relatively high strength, whereby the inner surface of the incontinent pad has a dry feel shortly after liquid is discharged thereon.

71. A diaper as in claim 70 wherein the lower surface of the bottom piling portion contacts and is supported by said barrier sheet.

72. A diaper as in claim 70 having a front portion and a back portion, the front portion being adapted to overlie the abdomen of an infant with its top edge generally in the area of the infant's navel button, characterized in that the means for securing the hygienic panel and the barrier sheet comprise
a relatively soft binding tape extending across the width of said top edge to minimize irritation of the belly button, and
impervious binding tape means secured to the remaining marginal edge portions of the hygienic panel and the barrier sheet.

73. A diaper as in claim 72 further characterized in that
the relatively soft binding tap is color coded to indicate the size of the diaper.

74. A diaper adapted to be worn by an incontinent in the fashion of a garment, said diaper including
a hygienic panel having an upper surface forming the inner surface of the diaper and adapted to contact the person of an incontinent and absorb liquid discharged by the incontinent,
a barrier sheet forming the outer, exterior surface of said pad and adapted to contain liquid discharged by the user, and
means for securing said hygienic panel and barrier sheet is superposed, assembled relation,
characterized in that
said hygienic panel has separate hydrophobic and hydrophilic properties, and comprises
a fabric constructed with
a top portion, of finite thickness, an outer portion of which defines the inner surface of the diaper,
a bottom portion of finite thickness, an outer portion of which defines the lower surface of the panel, and
a central portion in which inner end portions of the top and bottom portions are intermeshed,
said top portion being characterized in that it is formed of hydrophobic yarns, inner end portions of which extend into the central portion,
said top portion being further characterized in that it is hydrophobic and wicks liquid from the upper surface of the fabric to the central portion and is incapable of retaining any substantial amount of liquid therein,
said bottom portion being further characterized in that it is formed of hydrophilic yarns, inner end portions of which extend into said central portion,
said bottom portion being further characterized in that it is formed of hydrophilic yarns, inner end portions of which extend into said central portion,
said bottom portion being further characterized in that it wicks liquid from the central portion into the remainder of the bottom portion and provides a reservoir function in retaining the liquid,
further characterized in that
a hydrophobic yarn of the top portion essentially consists of a texturized yarn comprised of continuous filaments of a polymeric material, and
the ground yarn means has a relatively high strength, whereby, the upper surface of the panel has a dry feel shortly after liquid is discharged thereon.

75. A diaper as in claim 74 wherein the hygienic panel is further characterized in that
the inner end portions of the hydrophobic and hydrophilic yarns and the ground yarn of the central portion are knitted together in overlapping juxtaposition with each other, and
said central portion has a high density of yarns which facilitates dispersal of liquid from the top portion into the bottom portion and further provides a barrier inhibiting reverse flow of liquid therethrough, thereby minimizing passage of liquid from the bottom portion of the top portion as a result of pressures on the hygienic panel,
the ground yarn means is hydrophilic and has a relatively high strength.

76. A diaper as in claim 75 wherein the hygienic panel is further characterized in that
the ground yarn means are comprised of a yarn consisting of polymeric fiber staples and natural fiber staples.

77. A diaper as in claim 75 wherein the hygienic panel is further characterized in that
the ground yarn means comprise
a first ground yarn formed of polymeric filaments and
a second ground yarn formed of natural fiber staples.

78. A diaper as in claim 75 further characterized in that
the hygienic panel and barrier sheet have Y-shaped outlines defining
a front portion at one free end thereof,
a back portion at the opposite free end thereof, and
wing portions extending outwardly from opposite sides of the back portion,
said diaper being adapted to embrace the lower, crotch portion of a user's torso, with the front and back portions, respectively, in engagement with the front and back of the torso and further with the wing portions wrapped around the urser's torso into overlapping relation with the front portion,
said diaper further comprising
means for releasably fastening the respective, overlapping wing and back portions,
further characterized in that
the front and back portions compositely form a rectangle having a length (L), between the top free edge of the back portion and the bottom free edge of the front portion, which is approximately twice its width (W),
the outer ends of the wing portions are convexly curved from the free edge of the back portion and are further defined by concavely curved portions which extend from the approximate juncture of the front and back portions of the sheet member, and
the wing portions project from said rectangle a distance (A) approximately three tenths of the rectangle width (0.3 W), at a distance (B) from the free end of the back portion which is one tenth of the rectangle length (0.1 L).

79. A diaper as in claim 78 further characterized by gathered, elasticized portions of the hygienic panel and barrier sheet,
said gathered, elasticized portions being formed in the marginal side edge portions of the sheet member and extending from a point spaced inwardly of the free end of the front portion approximately to the juncture of the convexly and concavely curved portions of the wings,
said gathered, elasticized portions also being formed in the free end of the back portion.

80. A diaper as in claim 74 wherein the hygienic panel is further characterized in that
the top and bottom portions are in the form of pilings, and
the top portion piling comprises uncut loops defining the top surface of the hygienic panel, and
said top portion piling is brushed.

81. A diaper as in claim 80 wherein the hygienic panel is further characterized in that the top portion piling is medium brushed to a degree insufficient for liquid to "bead up" on its surface as a result of the surface tension of liquid impinged thereon.

82. A diaper as in claim 74 wherein the hygienic panel is further characterized in that
the bottom portion hydrophilic yarn piling approximates fifty percent of the fabric weight,
the top portion hydrophobic yarn comprises at least 30% of the weight of the fabric and
the balance of the fabric weight is formed by the ground yarn means.

83. A diaper as in claim 82 wherein the hygienic panel is further characterized in that
the top portion, hydrophobic yarn weight is approximately 3.3 ounces per square yard.

84. A diaper as in claim 74 wherein the hygienic panel is further characterized in that
the weight of the fabric is between about 7 and 13.5 ounces per square yard.

85. A diaper as in claim 74 wherein the hygienic panel is further characterized in that
the hydrophobic yarn is a textured yarn comprising continuous polyester filaments,
the hydrophilic yarn comprises spun cotton staples,
the bottom portion hydrophilic yarn piling approximates fifty percent of the fabric weight,
the top portion hydrophobic yarn comprises at least 30% of the weight of the fabric and
the balance of the fabric weight is formed by the ground yarn means.

86. A diaper as in claim 85 wherein the hygienic panel is further characterized in that
the top portion, hydrophobic yarn weight is approximately 3.3 ounces per square yard.

87. A diaper as in claim 85 wherein the hygienic panel is further characterized in that
the weight of the fabric is between about 7 and 13.5 ounces per square yard.

88. A diaper as in claim 87 wherein the hygienic panel is further characterized in that
the weight of the fabric is approximately 7.5 ounces per square yard,
the denier of the hydrophilic yarn is approximately 226/1,
the denier of the hydrophobic yarn is approximately 336/136,
the weight of the hydrophilic yarn is approximately 49% of the weight of the fabric,
the weight of the hydrophobic yarn is approximately 45% of the weight of the fabric, and
the balance of the weight of the fabric is comprised of the ground yarn means.

89. A diaper as in claim 88 wherein the hygienic panel is further characterized in that
the ground yarn means comprises multifilament polyester yarn having a denier of approximately 70/34.

90. A diaper as in claim 89 wherein the hygienic panel is further characterized in that
the fabric is a three bar, warp knit fabric.

91. A diaper as in claim 89 wherein the hygienic panel is further characterized in that
the hydrophobic yarn piling is formed by a pair of textured polyester yarns, each having a denier of approximately 168/68.

92. A diaper as in claim 87 wherein the hygienic panel is further characterized in that
the weight of the fabric is approximately 10.5 ounces per square yard,
the denier of the hydrophilic yarn is approximately 886/1,
the denier of the hydrophobic yarn is approximately 336/136,
the weight of the hydrophilic yarn is approximately 45% of the weight of the fabric,
the weight of the hydrophobic yarn is approximately 30% of the weight of the fabric, and
the balance of the weight of the fabric is comprised of the ground yarn means.

93. A diaper as in claim 92 wherein the hygienic panel is further characterized in that
the ground yarn means comprises
a first multifilament, non-texturized polyester ground yarn having a denier of approximately 70/34, and
a second spun ground yarn comprising 50% cotton staples and 50% polyester fibers having a denier of 332/1.

94. A diaper as in claim 93 wherein the hygienic panel is further characterized in that
the second ground yarn comprises approximately 20% of the weight of the fabric.

95. A diaper as in claim 93 wherein the hygienic panel is further characterized in that
the fabric is a four bar, warp knit fabric.

96. A diaper as in claim 93 wherein the hygienic panel is further characterized in that
said top portion piling is brushed.

97. A diaper as in claim 93 wherein the hygienic panel is further characterized in that
the hydrophobic yarn piling is formed by a pair of textured polyester yarns, each having a denier of approximately 168/68.

98. A diaper comprising
a hygienic panel
a barrier sheet, and
means securing the panel and barrier sheet is superposed relation,
said panel and barrier sheet is superposed relation,
said panel and barrier sheet compositely forming
a front portion and
a back portion,
the front portion being adapted to overlie the abdomen of an infant with its top edge generally in the area of the infant's navel button,
characterized in that
the means for securing the hygienic panel and the barrier sheet comprises
a relatively soft binding tape extending across the width of said top edge to minimize irritation of the belly button, and
impervious binding tape means secured to the remaining marginal edge portions of the hygienic panel and the barrier sheet.

99. A diaper as in claim 98 further characterized in that
the relatively soft binding tape is color coded to indicated the size of the diaper.

* * * * *